(12) United States Patent
Yonehara et al.

(10) Patent No.: US 8,637,275 B2
(45) Date of Patent: Jan. 28, 2014

(54) POSTPRANDIAL HYPERGLYCEMIA MARKER, METHOD OF MEASURING THE SAME, AND USAGE THEREOF

(75) Inventors: Satoshi Yonehara, Kyoto (JP); Toshihiro Imai, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 365 days.

(21) Appl. No.: 12/376,914

(22) PCT Filed: Aug. 10, 2007

(86) PCT No.: PCT/JP2007/065768
§ 371 (c)(1),
(2), (4) Date: Feb. 9, 2009

(87) PCT Pub. No.: WO2008/018596
PCT Pub. Date: Feb. 14, 2008

(65) Prior Publication Data
US 2010/0190194 A1 Jul. 29, 2010

(30) Foreign Application Priority Data
Aug. 11, 2006 (JP) .................................. 2006-220678

(51) Int. Cl.
*C12P 21/04* (2006.01)
(52) U.S. Cl.
USPC ....................................................... 435/69.6
(58) Field of Classification Search
USPC ............................................................. 435/69.6
See application file for complete search history.

(56) References Cited

U.S. PATENT DOCUMENTS

| | | | |
|---|---|---|---|
| 5,294,336 A | 3/1994 | Mizuno et al. | |
| 5,474,677 A | 12/1995 | Naka | |
| 5,948,659 A * | 9/1999 | Kato et al. | 435/189 |
| 7,235,378 B2 | 6/2007 | Yonehara | |
| 2003/0162242 A1 | 8/2003 | Yonehara | |

FOREIGN PATENT DOCUMENTS

| | | | |
|---|---|---|---|
| CN | 1620512 A1 | 5/2005 | |
| EP | 1176191 | 1/2002 | ............... C12N 9/48 |
| EP | 1 626 088 | 2/2006 | |
| EP | 1 878 801 | 1/2008 | |
| JP | 2001-057897 | 3/2001 | |
| JP | 2001-264336 | 9/2001 | |
| JP | 2005-062067 | 3/2005 | |
| WO | 02/06519 | 1/2002 | |

OTHER PUBLICATIONS

Makita et al. "Radioimmunoassay for the determination of glycated haemoglobin", Diabetologia, 1991, 34:40-45.*
Fonseca et al. "Redefining the diagnosis of diabetes using glycated hemoglobin", Diabetes Care, 2009, 32(7):1344-1345.*
Cohen et al. "Relationship of prospective GHb to glycated serum proteins in incident diabetic retinopathy", Diabetes Care, 2008, 31(1):151-153.*
Aminopeptidase definition: 1 page.*
Hassan et al., "The relationship between 24-hour integrated glucose concentrations and % glycohemoglobin", Journal of Laboratory and Clinical Medicine, vol. 147, No. 1, Jan. 2006, pp. 21-26.
Zhang et al., "Characterization of glycated hemoglobin in diabetic patients: usefulness of electrospray mass spectrometry in monitoring the extent and distribution of glycation", Journal of Chromatography B: Biomedical Sciences and Applications, vol. 759, Issue 1, Aug. 2001, pp. 1-15.
Shapiro et al., "Sites of Nonenzymatic Glycosylation of Human Hemoglobin A", Journal of Biological Chemistry, vol. 255, No. 7, Apr. 1980, pp. 3120-3127.
Kuzuya et al., "Report of the Committee of Japan Diabetes Society on the Classification and Diagnostic Criteria of Diabetes Mellitus", Journal of the Japan Diabetes Society, vol. 42, No. 5, 1999, pp. 385-404.
Kunika et al., "Affinity column chromatography, the $3^{rd}$ report: Synthesis of total glycated hemoglobin(T-GHb) or $GH b\alpha_{Lf}\beta_L$(T-GHb-$HbA_{1C}$) with the larger increase in response to hyperglycemia than $HbA_{1C}$", Japanese Journal of Medical Technology, vol. 39, No. 10, 1990, pp. 1559-1565.
Kunika et al., "Affinity column chromatography, the 1st report: Highly sensitive total glycohemoglobin(T-GHb) assay measuring glycation of valine and lysine residues", Japanese Journal of Medical Technology, vol. 39, No. 8, 1990, pp. 1272-1277, with its partial translation.
Supplementary European Search Report issued in corresponding European Application No. 07 79 2412.4, mailed Mar. 23, 2010—11 pages.

(Continued)

*Primary Examiner* — Bin Shen
(74) *Attorney, Agent, or Firm* — Morgan, Lewis & Bockius LLP

(57) ABSTRACT

A new method of diagnosing postprandial hyperglycemia by indirectly measuring a blood glucose level is provided. Postprandial hyperglycemia is detected by measuring a glycation degree of lysine in hemoglobin, in which a side chain amino group of lysine is glycated (GHbLys %). Measurement of GHbLys % can be performed by cleaving hemoglobin by protease, treating a glycated part of a lysine residue in the obtained cleavage product of hemoglobin with fructosyl amino acid oxidase, and measuring a redox reaction between the glycated part and fructosyl amino acid oxidase.

3 Claims, 4 Drawing Sheets

(56) References Cited

OTHER PUBLICATIONS

Ahmed, et al., "Glycated and Oxidized Protein Degradation Products are Indicators of Fasting and Postprandial Hyperglycemia in Diabetes", Diabetes Care, 2005, vol. 28, No. 10, pp. 2465-2471.

Shapiro, et al., "Nonenzymatic Glycosylation of Human Hemoglobin at Multiple Sites", Metabolism, 1979, vol. 28, No. 4, Suppl. 1, pp. 427-430.

Tegos, et al., "Glycosylated Minor C, D, and E Hemoglobins", Biochemical Medicine, 1981, vol. 26, No. 1, pp. 121-125.

Ahmed, et al., "Degradation products of proteins damaged by glycation, oxidation and nitration in clinical type 1 diabetes", Diabetologia, 2005, vol. 48, No. 8, pp. 1590-1603.

Haney, et al., "Glycosylation of Hemoglobin in vitro: Affinity labeling of hemoglobin by glucose-6-phosphate", Proceedings of the National Academy of Sciences of the United States of America, 1976, vol. 73, No. 10, pp. 3534-3538.

Rendell, et al., Inhibition of glycation of albumin and hemoglobin by acetylation in vitro and in vivo, Journal of Laboratory and Clinical Medicine, 1986, vol. 108, No. 4, pp. 286-293.

The partial European Search Report issued Apr. 20, 2011 in the corresponding European patent application No. 11156454.8.

Chinese Office Action issued in corresponding Chinese Patent Application No. 200780029943.5 dated Apr. 12, 2012.

The corrected version of the Extended European Search Report issued on Aug. 3, 2011 in the corresponding European Application No. 11156454.8.

Beisswenger et al., "α-Dicarbonyls increase in the postprandial period and reflect the degree of hyperglycemia", Diabetes Care, Apr. 1, 2001, vol. 24, No. 4, pp. 726-732.

Bastyr, III E J et al., "Targeting postprandial blood glucose concentrations reduced hemoglobin A1c concentrations in type 2 diabetes mellitus", Evidence-Based Medicine (English Edition), BMJ Group, May 1, 2001, vol. 6, No. 3, p. 80.

O'Sullivan et al., "Haemoglobin A1c (HbA1C) in Non-diabetic and Diabetic Vascular Patients. Is HbA1C and Independent Risk Factor and Predictor of Adverse Outcome?", European Journal of Vascular and Endovascular Surgery, Saunders, Aug. 1, 2006, vol. 32, No. 2., pp. 188-197.

Office Action issued in corresponding Chinese Patent Application No. 200780029943.5 dated Oct. 10, 2013.

\* cited by examiner

POSTPRANDIAL HYPERGLYCEMIA MARKER, METHOD OF MEASURING THE SAME, AND USAGE THEREOF

TECHNICAL FIELD

The present invention relates to a postprandial hyperglycemia marker, a method of detecting the same, and usage thereof.

BACKGROUND ART

As an indicator for showing a biological state, measurement of a glycation degree is performed with respect to glycation products of various kinds of proteins. Among them, a glycation product of hemoglobin (Hb) in a blood cell (hereinafter, also referred to as "Hb glycation product") is considered as an important indicator in diagnoses, treatments and the like for diabetes. Examples of the Hb glycation product include a product in which glucose is bonded to an α-amino group of a β chain N-terminal amino acid (valine) residue in Hb (hereinafter, also referred to as "HbA1c"); a product in which glucose is bonded to a side chain amino group of a lysine residue in Hb (hereinafter, also referred to as "GHbLys"); a product in which glucose is bonded to a side chain amino group of an arginine residue in Hb; etc. It is known that, in particular, HbA1c reflects histories (about 1 to 2 months) of an in-vivo blood glucose level, specifically, the usual average value of blood glucose level in past. An HbA1c value (HbA1c %) normally is represented by a ratio (%) of an HbA1c amount relative to a total Hb amount (or total HbA amount), and is, for example, referred to as a glycation degree of a β chain N-terminal amino acid residue in Hb or a glycation degree of a β chain N-terminal amino group.

In recent years, the detection of postprandial hyperglycemia, which is an early stage of diabetes, is emphasized. Postprandial hyperglycemia is a symptom in which even though a blood glucose level in the fasting state is within the normal range (110 mg/dL or less), the blood glucose level increases 1 to 2 hours after a meal. Generally, 2 hours after a meal, the blood glucose level increases to 140 mg/dL or more. If this postprandial hyperglycemia is left untreated, there is a possibility of developing full-blown diabetes or a possibility of increasing a risk for complication, cerebral infarction, and myocardial infarction. Therefore, it is important to detect postprandial hyperglycemia for preventing diabetes and the like. However, with respect to a sugar tolerance test adopted as a detecting method for postprandial hyperglycemia, for example, the patients have to handle the following burdens. First, for the sugar tolerance test, patients should fast at least 8 hours (for example, at least 14 hours) before the test, and then take 75 g of starch hydrolysate (glucose) for test in the fasting state. Further, because the change of postprandial hyperglycemia is fast, a blood glucose level should be measured by collecting blood 30 minutes, 60 minutes, and 120 minutes after the test as well as before the test. Moreover, since glucose digestion due to hemocyte cell occurs in the collected blood sample, the test should be performed in an institution capable of performing a prompt measurement. From these reasons, a direct measurement of glucose in the blood for detecting postprandial hyperglycemia forces time and physical burdens on patients. A method of indirectly judging postprandial hyperglycemia rather than a direct method is desired.

However, although HbA1c is a very effective indicator in diagnoses for diabetes, since HbA1c reflects an average value of blood glucose level in the past 1 to 2 months after all, postprandial hyperglycemia could not be detected from HbA1c as an indicator. This may be because of the following reasons. Specifically, in short-time rise in blood sugar, unstable HbA1c that is a precursor of the HbA1c was generated promptly. However, it is difficult to generate stable HbA1c from the unstable HbA1c. Therefore, it is considered that, on the basis of measurement of the stable HbA1c, although chronic diabetes can be judged, postprandial hyperglycemia, which shows hyperglycemia only after a meal, cannot be judged (Nonpatent Document 1). More specifically, the stable HbA1c shows the usual average value of blood glucose level in past and does not reflect intraday changes in blood glucose level affected by meals. Therefore, the stable HbA1c cannot be an indicator to grasp postprandial hyperglycemia. Further, with respect to the unstable HbA1c, since the measurement itself is difficult, it is not practical to judge postprandial hyperglycemia on the basis of the measurement of the unstable HbA1c.

[Nonpatent Document 1] Journal of Laboratory and Clinical Medicine, Vol 147, 1, 1-2006, p21-26

DISCLOSURE OF THE INVENTION

Hence, an object of the present invention is to provide a new postprandial hyperglycemia marker and a method of detecting the same for indirectly detecting postprandial hyperglycemia with the marker.

The present invention is a postprandial hyperglycemia marker for diagnoses for postprandial hyperglycemia and contains hemoglobin having a glycated lysine residue (hereinafter, also referred to as "GHbLys").

A method of measuring a postprandial hyperglycemia marker of the present invention is a method of measuring a glycation degree of a lysine residue in hemoglobin (hereinafter, also referred to as "Hb"), the marker being a postprandial hyperglycemia marker of the present invention (GHbLys).

A method of determining a risk of the present invention is a method of determining a risk for a specimen to develop diabetes and comprises the following process (a).

(a) a process of measuring a postprandial hyperglycemia marker GHbLys of the present invention by measuring a glycation degree of a lysine residue in Hb by a method of measuring of the present invention with respect to a blood sample obtained from the specimen.

A method of diagnosing of the present invention is a method of diagnosing postprandial hyperglycemia of a specimen and comprises the following process (c).

(c) a process of measuring a postprandial hyperglycemia marker GHbLys of the present invention by measuring a glycation degree of a lysine residue in Hb by a method of measuring of the present invention with respect to a blood sample obtained from the specimen.

A method of measuring an average blood glucose level of the present invention is a method of measuring an average blood glucose level reflecting a postprandial blood glucose level and comprises the following processes (x) and (y).

(x) a process of measuring an average blood glucose level marker measuring a glycation degree of a lysine residue in Hb by a method of measuring a postprandial hyperglycemia marker of the present invention with respect to a blood sample obtained from a specimen, the average blood glucose level marker being a postprandial hyperglycemia marker of the present invention; and (y) a process of calculating the average blood glucose level reflecting a postprandial blood glucose level by substituting the glycation degree of the lysine residue in Hb measured in the process (x) to a relational expression between a glycation degree of a lysine residue in Hb and an average blood glucose level reflecting a postprandial blood glucose level.

A kit for measuring a marker of the present invention is a kit used for a method of measuring a postprandial hyperglycemia marker of the present invention and comprises protease, fructosyl amino acid oxidase, peroxidase, and a substrate developing a color by oxidation. Further, the kit for measuring a marker of the present invention can be used for a method of measuring an average blood glucose level of the present invention.

A kit for determining a risk of the present invention is a kit used for a method of determining a risk of developing diabetes of the present invention and comprises protease, fructosyl amino acid oxidase, peroxidase, and a substrate developing a color by oxidation.

A kit for diagnosing postprandial hyperglycemia of the present invention is a kit used for a method of diagnosing postprandial hyperglycemia of the present invention and comprises protease, fructosyl amino acid oxidase, peroxidase, and a substrate developing a color by oxidation.

As a result of keen studies made assiduously, the inventors found out for the first time that a glycation degree of hemoglobin (GHbLys) having a glycated side chain amino group of a lysine residue shows a relational expression with postprandial hyperglycemia. HbA1c, which is a kind of glycated Hb, is generated gently in response to a movement of a blood glucose level, for example. Therefore, if the hyperglycemia is not maintained for several hours (for example, 5 to 12 hours), generation of the aforementioned stable HbA1c is difficult and an increase in an HbA1c value (HbA1c %) is not confirmed. Thus, with respect to the measurement of HbA1c, although histories of a blood glucose level in past 1 to 2 months are indirectly detected, postprandial hyperglycemia could not be detected. In contrast, it was found by the inventors of the present invention that GHbLys is generated sensitively in response to a hyperglycemia state even for a short time such as several tens of minutes to 2 hours after a meal, and an increase of GHbLys amount correlates with an increase in blood glucose. From this new insight, postprandial hyperglycemia could be found indirectly by measuring a glycation degree of GHbLys serving as a postprandial hyperglycemia marker. Postprandial hyperglycemia is so-called borderline diabetes, and the sufficient prevention at this stage allows delay and prevention of the development of diabetes as well as suppression of complications. Therefore, when GHbLys serving as the postprandial hyperglycemia marker is detected according to the present invention, for example, it can be judged whether one is postprandial hyperglycemia. Further, the measurement of the postprandial hyperglycemia marker GHbLys of the present invention makes it possible to determine the risk for developing diabetes, that is, the possibility of developing from the early stage to the later stage. Accordingly, it can be said that the present invention is very effective for diagnosis of postprandial hyperglycemia and prevention of the development of diabetes.

BEST MODE FOR CARRYING OUT THE INVENTION

Postprandial Hyperglycemia Marker

Figure 1:
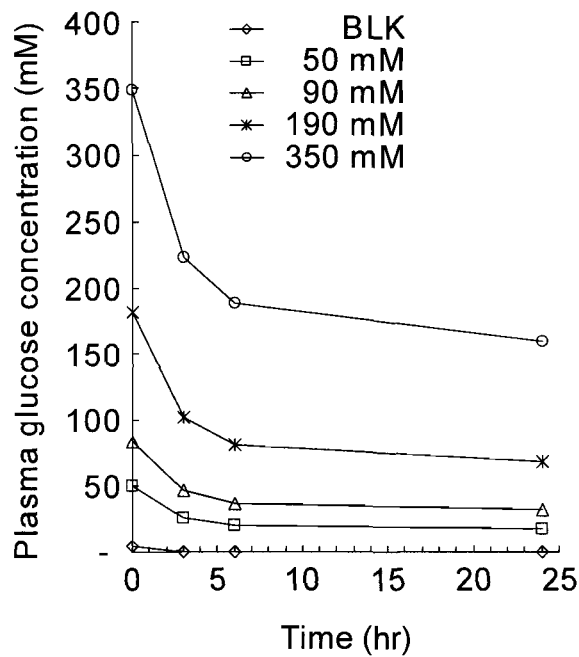
FIG. 1 is a graph showing a relationship between an incubation time of glucose added blood and a plasma glucose concentration in Example 1 of the present invention.

As described above, a postprandial hyperglycemia marker of the present invention is hemoglobin having a glycated lysine residue (GHbLys). Specifically, the postprandial hyperglycemia marker of the present invention is the Hb, a side chain amino group (e-amino group) of a lysine residue thereof is glycated. As described above, the inventors of the present invention found for the first time that GHbLys in a sample is an indicator of the postprandial hyperglycemia marker. By regarding this GHbLys as the postprandial hyperglycemia marker, it can be judged whether one is postprandial hyperglycemic. Further, the degree of postprandial hyperglycemia and a risk for diabetes (development to the middle stage and the later stage) can be judged.

In the present invention, GHbLys is also an average blood glucose level marker that reflects a postprandial blood glucose level. As described above, HbA1c is an indicator that shows histories of a blood glucose level in past, however is correlated with the usual average value of a blood glucose level and does not reflect intraday changes. Therefore, even in a case where the blood glucose level is increased after a meal (in a case of postprandial hyperglycemia), the fact is not reflected in the usual average value indicated by HbA1c. In contrast, the inventors of the present invention found that GHbLys serves as an indicator of an average blood glucose level that reflects a postprandial blood glucose level. Therefore, as described later, for example, it can be judged whether one is postprandial hyperglycemic by calculating an average blood glucose level that reflects a postprandial blood glucose level by measuring the marker GHbLys of the present invention.

<Measurement of Postprandial Hyperglycemia Marker>

As described above, with respect to a method of measuring a postprandial hyperglycemia marker of the present invention, the marker is a postprandial hyperglycemia marker of the present invention and the measurement of the postprandial hyperglycemia marker is a measurement of a glycation degree of a lysine residue in Hb.

In the present invention, a glycation degree of a lysine residue in Hb normally means a ratio (%) of Hb having a glycated lysine residue relative to a total Hb. More specifically, the glycation degree of the lysine residue in Hb normally means a ratio of an amount (or a concentration) of Hb having a glycated lysine residue relative to a total amount (or a concentration) of Hb. Further, as described above, since GHbLys is Hb having a glycated lysine residue, in the present invention, it can be said that the glycation degree of the lysine residue in Hb is a GHbLys value. In the present invention, the glycation degree serving as the GHbLys value is referred to as GHbLys %.

In the present invention, the expression of "total Hb" may mean Hb in general including HbA, HbA2, HbF, etc., or may mean total HbA. The total Hb includes both non-glycated Hb and glycated Hb, for example. Further, in the present invention, the total Hb may be a total lysine residue in Hb or a specific lysine residue in Hb. Also in this state, the total Hb includes both non-glycated Hb and glycated Hb.

In the present invention, the expression of "Hb having a glycated lysine residue" means HbA having a glycated lysine residue. Further, "Hb having a glycated lysine residue" may be a glycated lysine residue in Hb or a specific glycated lysine residue in Hb. In other words, the glycation degree may mean a ratio of the glycated lysine residue relative to the total lysine residue in Hb, or may mean a ratio of the specific glycated lysine residue relative to the specific lysine residue in Hb.

GHbLys % can be calculated with the following Formula, for example.

$$GHbLys\% = (GHbLys/\text{total } Hb) \times 100$$

In the Formula, GHbLys includes a GHbLys amount (for example, a Hb lysine residue glycation amount) or a GHbLys concentration (for example, a Hb lysine residue glycation concentration). Total Hb includes a total Hb amount or a Hb concentration, or includes a total HbA amount or a HbA concentration. On the basis of the aforementioned Formula, GHbLys % can be obtained by calculating a ratio (percent) between a glycation amount of a lysine residue in Hb (glycation concentration of a lysine residue in Hb) and a total Hb amount (Hb concentration) or a total HbA amount (HbA concentration) in a sample.

As described above, postprandial hyperglycemia is a symptom in which the blood glucose level increases 1 to 2 hours after a meal, and normally is divided into diabetes with at least 200 mg/dL and borderline diabetes with at least 140 mg/dL. According to a method of measuring of the present invention, it can be judged whether one is postprandial hyperglycemic by measuring the postprandial hyperglycemia marker GHbLys of the present invention instead of a blood glucose level (glucose concentration) at about 1-2 hours after a meal. Further, as described above, by measuring the postprandial hyperglycemia marker GHbLys, it can be converted into an average blood glucose level reflecting a postprandial blood glucose level.

In the present invention, it is clarified that GHbLys % shows a correlation with postprandial hyperglycemia, that is, postprandial hyperglycemia can be detected by measuring GHbLys %. Therefore, a method of measuring GHbLys % itself is not limited at all and can adopt conventionally known measuring methods. Examples of the method of measuring GHbLys % include a high-performance liquid chromatography (HPLC) method, an immunization method, an enzymatic method, an electrophoresis method, a mass spectrometry method, etc.

A method of measuring GHbLys % by the enzymatic method is explained below as an example. However, the present invention is not limited thereto.

The method of measuring GHbLys % by the enzymatic method comprises the following processes (A) to (C), for example. In the following, the target to be cleaved by protease is referred to as "Hb". This "Hb" also includes glycated Hb. Further, lysine and peptide having lysine residue obtained as a cleavage product also include glycated lysine and peptide having glycated lysine residue.

(A) a process of cleaving Hb by protease (B) a process of treating a glycated part of a lysine residue in obtained cleavage product of Hb with fructosyl amino acid oxidase (hereinafter, referred to as "FAOD"); and (C) a process of determining a glycation degree of a lysine residue in Hb by measuring a redox reaction between the glycated part and FAOD.

(A) Protease Treatment

The cleavage product cleaved from Hb by protease normally include lysine, lysine which is glycated (glycated lysine), peptide containing a lysine residue (lysine peptide), or peptide containing a glycated lysine residue (glycated lysine peptide). As for lysine residues, glycation thereof is confirmed in Hb, for example, the $61^{st}$, the $40^{th}$, the $7^{th}$, the $16^{th}$, the $139^{th}$, and the $127^{th}$ of an α chain and the $66^{th}$, the $17^{th}$, the $8^{th}$, the $61^{st}$, the $65^{th}$, the $132^{nd}$, the $144^{th}$ etc. of a β chain are reported. Among them, the $61^{st}$, the $40^{th}$, and the $127^{th}$ of the α chain and the $66^{th}$ and the $17^{th}$ of the β chain are particularly effective for measurement of the glycation degree (X. Zhang et al., J. Chromatogr. B759 (2001) 1-15, R. Shapiro et al., J. Biol. Chem. 255 (1980) 3120). A cleavage pattern of Hb by the protease treatment is not limited and can be decided suitably according to the protease to be used, for example. The length of peptide to be cleaved is not limited and can be set suitably according to the protease. Specifically, the number of an amino acid residue is, for example, 2 to 6, and preferably 2 to 4. A sequence of peptide to be cleaved varies according to types of the protease, for example. In the case of peptide containing the $127^{th}$ lysine of the α chain, examples of the sequence include Leu-Asp-Lys-Phe, Leu-Asp-Lys, etc.

Examples of the protease include metalloprotease, serine protease, serine carboxypeptidase, proteinase K, bromelain, papain, trypsin derived from porcine pancreas, protease derived from *Bacillus subtilis*, protease derived from *Aspergillus oryzae* and the like, and endoprotease is preferably used. Commercially available products that can be used for the protease include, for example, metalloprotease, manufactured by Arkray, Inc.; protease A "Amano" G, manufactured by Amano Enzyme Inc.; protease M "Amano" G, manufactured by Amano Enzyme Inc.; protease S "Amano" G, manufactured by Amano Enzyme Inc.; peptidase R, manufactured by Amano Enzyme Inc.; papain M-40, manufactured by Amano Enzyme Inc.; protease N (trade name) manufactured by Fluka Chemie AG; protease N "Amano" (trade name) manufactured by Amano Enzyme Inc.; metalloproteinase derived from the genus *Bacillus* manufactured by Toyobo Co., Ltd. under a trade name of Toyoteam; etc.

In a case where lysine or glycated lysine, or lysine peptide or glycated lysine peptide is cleaved, for example, the protease described in International Publication WO2002/006519 is preferably used. Use of these proteases, in the presence of the cleavage acceleration compound described later, make it possible to perform distinctly prompt and specific Hb cleavage.

For example, Hb cleavage can be performed by adding protease to a sample containing Hb.

A ratio of protease to be added in a reaction solution for the protease treatment is, for example, in the range of 0.001 to 300,000 KU/L, preferably in the range of 0.01 to 30,000 KU/L, and particularly preferably in the range of 0.1 to 10,000 KU/L. In a case where a concentration of Hb in the aforementioned reaction solution is 0.005 mM, a ratio of protease to be added is, for example, in the range of 0.01 to 300,000 KU/L, preferably in the range of 0.05 to 30,000 KU/L, and particularly preferably in the range of 0.1 to 10,000 KU/L. With respect to an activity of protease "U", an amount of enzyme that applies an increase of absorbance of 275 nm per minute that is equivalent to that of a micromole of tyrosine is defined as 1U.

The protease treatment preferably is performed, for example, in a buffer solution. As the buffer solution, a Tris-HCL buffer solution, an EPPS buffer solution, a PIPES buffer solution, a phosphoric acid buffer solution, an ADA buffer solution, a citric acid buffer solution, an acetic acid buffer solution, a MES buffer solution, a MOPS buffer solution, an HEPES buffer solution, a malic acid buffer solution, and the like can be used. Further, pH of the reaction solution is, for example, in the range of 4 to 10 and preferably in the range of 6 to 9. The pH may be regulated by the aforementioned buffer solutions, for example.

Conditions of the protease treatment are not particularly limited. A treatment temperature is, for example, in the range of 10 to 40° C. and preferably in the range of 25 to 37° C. A treatment time is, for example, about 1 to 100 minutes and preferably 1 to 10 minutes.

The sample is not particularly limited as long as the sample contains Hb. Specifically, examples of the sample include a whole blood sample, a hemocyte sample, and a hemolyzed sample thereof. A method of hemolyzing a whole blood sample and a hemocyte sample is not limited. Examples of the method include a method using an osmolality gap, a method using an ultrasonic wave, etc. In a case of the method using the osmolality gap, the sample may be hemolyzed, for example, by adding purified water that is 2 to 100 times much as whole blood (or hemocyte) in volume. Further, the sample may be hemolyzed by adding a surfactant.

The protease treatment may be performed in the presence of the acceleration compound described below. When Hb is applied with the protease treatment in the presence of the acceleration compound, lysine and peptide may be cleaved in a short time. Therefore, the efficiency of the protease treatment can be increased and shortening of the protease treatment can be realized. Further, because an efficient protease treatment can be performed, for example, an increase of protease used for the treatment becomes unnecessary. Although the mechanism is unknown for efficiently cleaving lysine and peptide from Hb with the acceleration compound, it is expected that, because of the coexistence of the acceleration compound, the structure of Hb may be changed to the structure easily treated with protease.

An example of the acceleration compound includes a compound represented by the following Formula (I).

$$R-X \quad (I)$$

In the Formula (I), R represents an alkyl group, a substituted alkyl group, an acyl group, or a substituted acyl group with a carbon number of 9 or more. Specific examples include a straight-chain alkyl group or a straight-chain acyl group with a carbon number of 9 to 16, a branched-chain alkyl group or a branched-chain acyl group with a carbon number of 10 to 40 and a main-chain carbon number of 9 to 16, a straight-chain alkyl group that is substituted by cycloalkyl, and the like. For example, a carbon number of the cycloalkyl ranges from 3 to 8. With respect to the straight-chain alkyl group, it is preferable that a carbon number of the straight chain except for cycloalkyl ranges from 4 to 13. Examples of the cycloalkyl include cyclohexyl, cyclopenthyl, cyclobutyl and the like.

In the above Formula (I), X represents a sugar residue. The sugar residue is preferably a residue of a monosaccharide or a disaccharide, for example. Examples of the monosaccharide include mannoside, glucoside, thioglucoside and the like, and examples of the disaccharide include maltoside, fructopyranosyl-glucopyranoside, thiomaltoside and the like. Structures of these sugars may be any of α, β, D or L. Moreover, hydrogen to be bonded to a cyclic structure of the sugar and hydrogen in an OH group may be substituted by Na, K, halogen or the like, for example. Incidentally, in the present invention, atoms via which R and the cyclic structure of the sugar residue are bonded (for example, —O—, —S— and the like) are components of the sugar residue.

Examples of the acceleration compound of the Formula (I) include n-dodecyl-β-D-maltoside (n-dodecyl-β-D-maltopyranoside), 6-cyclohexylhexyl-β-D-maltoside, sucrose monolaurate (β-D-fructopyranosyl-α-D-glucopyranoside monododecanoate), n-decyl-β-D-maltoside (n-decyl-β-D-maltopyranoside), n-nonyl-β-D-thiomaltoside (n-nonyl-β-D-thiomaltoside), 5-cyclohexylpenthyl-β-D-maltoside, undecyl-β-D-maltoside, n-dodecyl-αβ-D-maltoside, hexadecyl-β-D-maltoside and 3-oxamidecyl-α-D-mannoside and the like. Chemical Formulae of these compounds are indicated later. One of the compounds may be used alone or two or more of them may be used in combination. Among them, n-dodecyl-β-D-maltoside, sucrose monolaurate, hexadecyl-β-D-maltoside and the like, whose carbon number of R (alkyl chain) in the above Formula (I) are 12 or more, are preferable. Moreover, in a case where the carbon numbers of R are the same (for example, the alkyl group and the acyl group that are the same in carbon number), the acyl group is more preferable, so that n-dodecyl-β-D-maltoside (n-dodecyl-β-D-maltopyranoside) is preferable.

[Chemical Formula 1]

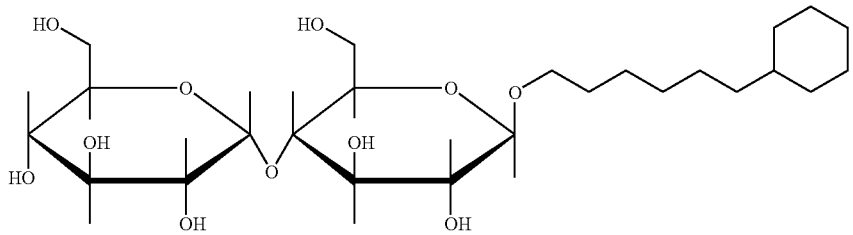

6-Cyclohexylhexyl-β-D-maltoside

-continued

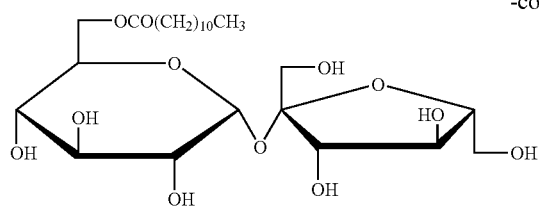
Sucrose monolaurate

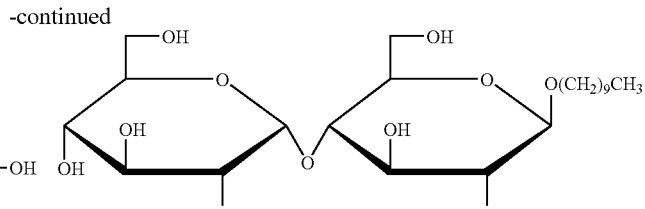
n-Decyl-β-D-maltoside

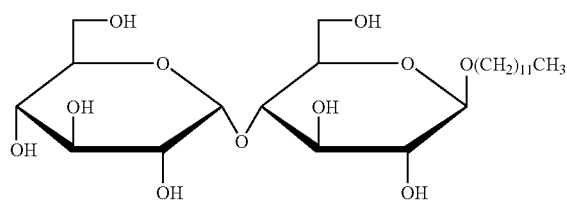
n-Dodecyl-β-D-maltoside

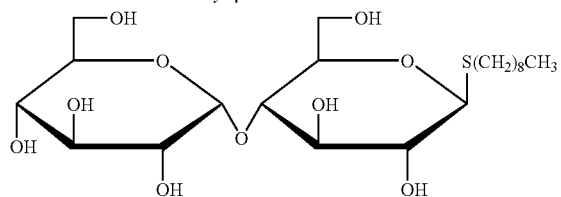
n-Nonyl-β-D-thiomaltoside

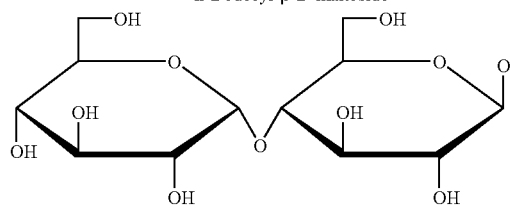
n-Hexadecyl-β-D-maltoside

[Chemical Formula 2]

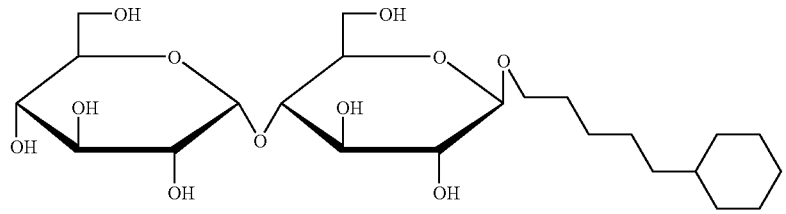
5-Cyclohexylpentyl-β-D-maltoside

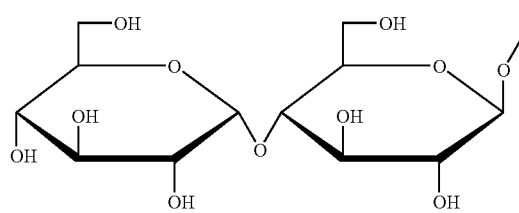
Undecyl-β-D-maltoside

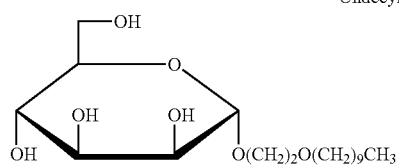
3-Oxatridecyl-α-D-mannoside

A ratio of the acceleration compound to be added in the reaction solution for the protease treatment is, for example, in the range of 0.01 to 200 mM and preferably in the range of 0.4 to 100 mM. When a Hb concentration in the reaction solution is 0.005 mM, a ratio of the acceleration compound to be added is, for example, in the range of 0.4 to 100 mM and preferably in the range of 1 to 100 mM. In this state, an addition order of the acceleration compound and protease is not limited at all. They can be added simultaneously or in a random order.

In a case where the acceleration compound is coexisted, conditions of the protease treatment are not particularly limited as in the above. A treatment time is not limited. Particularly, the upper limit of the treatment time is not limited. For example, the protease treatment can be performed in 0.1 to 60 minutes. Specifically, the treatment time is preferably 0.1 to 45 minutes, more preferably 0.2 to 20 minutes, and particularly preferably 0.2 to minutes. When the protease treatment is performed in the presence of the acceleration compound, amino acid and peptide can promptly be cleaved, and therefore a cleavage treatment can sufficiently be performed within the aforementioned treatment time.

Besides the compound represented by the Formula (I), an example of the acceleration compound includes a nitro compound. One of nitro compounds may be used alone or two or more of them may be used in combination. Further, the nitro compound may be used in combination with the compound represented by the Formula (I). Examples of this nitro compound include nitrous acid and its salt. The nitrous acid is not particularly limited, and may be, for example, potassium nitrite, amyl nitrite, butyl nitrite, nitroglycerin, sodium nitrite, paranitrochlorbenzene, trinitrotoluene, nitrobenzene, and the like. A ratio of the nitro compound to be added in the reaction solution for the protease treatment is not particularly limited. For example, in a case where a Hb concentration in the reaction solution is 0.005 mM, the ratio of the nitro compound to be added is, for example, preferably 0.005 mM or more, and more preferably 0.05 to 2 mM. Further, as the acceleration compound, a tetrazolium compound may be used as described in WO02/27012.

In order to reduce an effect of a reducing substance such as ascorbic acid and protein in a sample, in advance of a FAOD treatment which is the next process, a tetrazolium compound preferably is added to the sample (for example, see JP2000-210100 A). The tetrazolium compound may be added before or after the protease treatment. The tetrazolium compound is not particularly limited and examples thereof include 2-(4-iodophenyl)-3-(4-nitrophenyl)-5-(2,4-disulfophenyl)-2H-tetrazolium salt, 2-(4-iodophenyl)-3-(2,4-dinitrophenyl)-5-(2,4-disulfophenyl)-2H-tetrazolium salt, 2-(2-methoxy-4-nitrophenyl)-3-(4-nitrophenyl)-5-(2,4-disulfophenyl)-2H-tetraz olium salt, 2-(4-iodophenyl)-3-(4-nitrophenyl)-5-phenyl-2H-tetrazolium salt, 3,3'-(1,1'-biphenyl-4,4'-diyl)-bis(2,5-diphenyl)-2H-tetrazolium salt, 3,3'-[3,3'-dimethoxy-(1,1'-biphenyl)-4,4'-diyl]-bis[2-(4-nitropenyl)-5-phenyl-2H-tetrazolium salt], 2,3-diphenyl-5-(4-chlorophenyl) tetrazolium salt, 2,5-diphenyl-3-(p-diphenyl)tetrazolium salt, 2,3-diphenyl-5-(p-diphenyl)tetrazolium salt, 2,5-diphenyl-3-(4-styrylphenyl)tetrazolium salt, 2,5-diphenyl-3-(m-tolyl)tetrazolium salt, 2,5-diphenyl-3-(p-tolyl)tetrazolium salt, 2,3-diphenyl-5-(2-thienyl)tetrazolium salt, 2-benzothiazoyl-3-(4-carboxy-2-methoxyphenyl)-5-[4-(2-sulfoethylcarbamoyl)p henyl]-2H-tetrazolium salt, 2,2'-dibenzothiazolyl-5,5'-bis[4-di(2-sulfoethyl)carbamoylphenyl]-3,3'-(3,3'-dim ethoxy-4,4'-biphenylene)ditetrazolium salt, 3-(4,5-dimethyl-2-thiazoyl)-2,5-diphenyl-2H-tetrazolium salt, 2,3-diphenyl-5-cyanotetrazolium salt, 2,3-diphenyl-5-carboxytetrazolium salt, 2,3-diphenyl-5-methyltetrazolium salt, 2,3-diphenyl-5-ethyltetrazolium salt, etc. Among them, 2-(4-iodophenyl)-3-(2,4-dinitrophenyl)-5-(2,4-disulfophenyl)-2H-tetrazolium salt is particularly preferable.

An amount of the tetrazolium compound to be added is not particularly limited. For example, the amount of the tetrazolium compound is preferably 0.001 to 100 μmol per μL of the sample, more preferably in the range of 0.005 to 30 μmol, and particularly preferably in the range of 0.01 to 10 μmol.

(B) FAOD Treatment

Next, the cleavage product of Hb obtained by the protease treatment is treated with FAOD. Thereby, FAOD is acted on a glycated part of a side chain amino group (ε-amino group) of lysine. Due to this FAOD treatment, for example, sugar bonded to the s-amino group of lysine is liberated and thereby hydrogen peroxide is generated.

FAOD used for the method of measuring GHbLys % is, at least, preferably an enzyme (FAOD-S) catalyzing a reaction shown in the Formula (1') by acting on amino acid or peptide whose amino group (for example, ε-amino group) of amino acid side chain is glycated.

$$R^1-CO-CH_2-NH-R^2+H_2O+O_2 \rightarrow R^1-CO-CHO+NH_2-R^2+H_2O_2 \qquad (1')$$

In Formula (1') above, $R^1$ represents a hydroxyl group or a residue derived from a sugar before a glycation reaction (i.e., sugar residue). The sugar residue ($R^1$) is an aldose residue when the sugar before the reaction is an aldose, and it is a ketose residue when the sugar before the reaction is ketose. For example, when the sugar before the reaction is a glucose, it takes a fructose structure after the reaction due to an Amadori rearrangement. In this case, the sugar residue ($R^1$) becomes a glucose residue (aldose residue). This sugar residue ($R^1$) can be represented, for example, by $$-[CH(OH)]_n-CH_2OH$$

wherein n is an integral number of 0 to 6.

In Formula (1') above, $R^2$ can be represented by the following Formula (4'). In the following Formula (4'), "—$(CH_2)_4$—" indicates a part of the side chain group of lysine except for the glycated amino group.

$$-(CH_2)_4-CH(NH-R^6)-CO-R^7 \qquad (4')$$

In Formula (4') above, $R^6$ represents hydrogen, an amino acid residue, or a peptide residue, and can be represented by the following Formula (5'). In the following Formula (5'), n is an integer of 0 or more, $R^3$ represents an amino acid side chain group, and the amino acid side chain groups may be either the same or different.

$$-(CO-CR^3H-NH)_n-H \qquad (5')$$

In Formula (4') above, $R^7$ represents a hydroxyl group, an amino acid residue, or a peptide residue, and can be represented by the following Formula (6'). In the following Formula (6'), n is an integer of 0 or more, $R^3$ represents an amino acid side chain group as in the above, and the amino acid side chain groups may be either the same or different.

$$-(NH-CHR^3-CO)_n-OH \qquad (6')$$

An example of FAOD-S specifically acting on the glycated amino acid side chain includes FAOD derived from the genus *fusarium* (Maki Fujiwara et al., "Conversion of substrate specificity of amino acid oxidase derived from *Fusarium oxysporum*", The Society for Biotechnology, Japan, 2000).

FAOD further may include substrate specificity besides that shown in Formula (1'). An example of such FAOD includes one that acts on both the glycated α-amino group and the glycated amino acid side chain group (hereinafter, referred to as "FAOD-αS"). Specific examples thereof include a commercially available product under the name of FOD (manufactured by Asahi Kasei Corporation), FAOD derived from genus *gibberella* (JP8-154672 A), FAOD derived from genus *fusarium* (JP7-289253 A), FAOD derived from genus *aspergillus* (WO99/20039 A1), etc. In a case of such FAOD, the protease described in International Publication WO2002/006519 preferably is used in combination therewith as the aforementioned protease. The aforementioned protease is protease hardly generating (liberating) amino acid, and an N-terminal α-position amino group thereof is glycated. In other words, the aforementioned protease is protease specifically cleaving lysine and peptide containing lysine. Combination of such protease with the FAOD-αS makes it possible to prevent FAOD from acting on the other glycated part (for example, a glycated part of the α-position amino group).

The catalytic reaction of FAOD acting on a glycated α-amino group is a reaction generating α-keto aldehyde and hydrogen peroxide by acting on amino acid, an α-amino group thereof is glycated, or peptide. This reaction is, in the Formula (1'), a reaction in which $R^2$ is represented by an amino acid residue or a peptide residue in the following Formula (2). Hereinafter, an enzyme catalyzing such reaction is referred to as "FAOD-α".

—CHR³—CO—R⁴ (2)

In Formula (2) above, $R^3$ represents an amino acid side chain group, and $R^4$ represents a hydroxyl group, an amino acid residue, or a peptide residue. $R^4$ can be represented by the following Formula (3), for example. In the following Formula (3), n is an integer of 0 or more, $R^3$ represents an amino acid side chain group as in the above, and the amino acid side chain groups may be either the same or different.

—(NH—CHR³—CO)ₙ—OH (3)

Preferably, a FAOD treatment is performed in a buffer solution in the same manner as the case of the protease treatment. The buffer solution is not particularly limited and the one similar to one used in the protease treatment can be used. Conditions of the FAOD treatment are not particularly limited. For example, pH of a reaction solution is 6 to 9 and a treatment temperature is, for example, in the range of 10 to 38° C., and preferably in the range of 25 to 37° C. A treatment time also is not particularly limited and is, for example, 0.1 to 60 minutes, and preferably 0.1 to 5 minutes.

A ratio of FAOD to be added in a reaction solution for the FAOD treatment is, for example, in the range of 0.01 to 50 KU/L, and preferably in the range of 0.5 to 10 KU/L. With respect to an activity of FAOD "U", an amount generating 1 micromole of hydrogen peroxide per minute by using fructosylvaline or fructosyl-lysine as a substrate is defined as 1U.

(C) Measurement of Redox Reaction

Next, measurement of a redox reaction between the glycated part and FAOD is performed. Examples of this measurement may include, for example, measurement of a hydrogen peroxide amount generated by the reaction and measurement of an oxygen amount that is consumed in the reaction. The hydrogen peroxide amount and the oxygen amount can be measured by conventionally known arts. For example, the hydrogen peroxide amount can be measured with peroxidase (POD) and a substrate that develops a color by oxidation (hereinafter, referred to as a chromogenic substrate). Specifically, the measurement of the hydrogen peroxide amount can be performed by developing the color of the substrate by the reaction between the chromogenic substrate and hydrogen peroxide with POD as a catalyst, and measuring a level of this color. Further, besides an enzyme method using POD, etc., the hydrogen peroxide amount can be measured by an electrical method, and the like.

The above-mentioned chromogenic substrate is not particularly limited and includes N-(carboxymethylaminocarbonyl)-4,4'-bis(dimethylamino) diphenylamine sodium (trade name: DA-64 manufactured by Wako Pure Chemical Industries, Ltd.), N,N,N',N',N'',N''-hexa(3-sulfopropyl)-4,4',4''-triaminotriphenylmethanehexaso dium salt (for example, trade name: TPM-PS manufactured by DOJINDO LABORATORIES), 10-(carboxymethylaminocarbonyl)-3,7-bis (dimethylamino)phenothiazine or its salt (for example, trade name: DA-67 manufactured by Wako Pure Chemical Industries, Ltd.), N-(carboxymethylaminocarbonyl)-4,4'-bis(dimethylamino) diphenylamine sodium, orthophenylendiamin (OPD), a substrate of a combination of Trinder's reagent and 4-aminoantipyrine, etc. The Trinder's reagent can be, for example, phenols, phenol derivatives, aniline derivatives, naphthols, naphthol derivatives, naphthylamine, naphthylamine derivatives or the like. Besides the 4-aminoantipyrine, it also is possible to use aminoantipyrine derivatives, vanillin diamine sulfonic acid, methylbenzothiazolinone hydrazone (MBTH), sulfonated methyl benzothiazolinone hydrazone (SMBTH), or the like.

POD reaction preferably is performed in a buffer solution in the same manner as the case of the protease treatment. As for the buffer solution, the aforementioned buffer solution may be used. Conditions of a POD treatment are not particularly limited. For example, pH of the reaction solution for the POD reaction is 5 to 9, and a treatment temperature is, for example, in the range of 10 to 40° C., preferably in the range of 25 to 37° C. A treatment time also is not particularly limited and is, for example, 0.1 to 5 minutes.

A ratio of POD to be added in the reaction solution is, for example, in the range of 0.01 to 300 KU/L and preferably in the range of 0.5 to 40 KU/L. Further, a ratio of the chromogenic substrate to be added in the reaction solution is, for example, in the range of 0.001 to 10 mM and preferably in the range of 0.005 to 2 mM. With respect to an activity of POD "U", an amount oxidizing 1 micromole of guaiacol per minute is defined as 1U.

In the case of using the chromogenic substrate, for example, the developed color (for example, an absorbance of the reaction solution) may be measured by a spectrophotometer. Specifically, the absorbance and a transmittance of the reaction solution may be measured. Further, a measurement wavelength is not limited and can be decided suitably according to types of the chromogenic substrate used, for example. The hydrogen peroxide amount (or hydrogen peroxide concentration) corresponds to a glycation amount (or glycation concentration) of lysine in Hb. Therefore, the glycation amount of lysine in Hb can be calculated from the measured absorbance. Then, as shown in the following Formula, by calculating a ratio (percent) between this glycation amount (or glycation concentration) of lysine in Hb and a total Hb amount (Hb concentration) in a sample, GHbLys % can be obtained. Incidentally, the total Hb amount can be measured by a conventionally known method or by a commercially available reagent kit.

GHbLys%=(glycation amount of lysine in *Hb*/total *Hb* amount)×100

The glycation amount of lysine in Hb can be calculated from the absorbance, using a standard curve. For example, the standard curve is obtained by plotting a relationship between the known glycation amount of lysine in Hb and the absorbance. For example, with respect to Hb reference material whose glycation amount of lysine is known, the absorbance measurement is performed in the same manner as described above, and a standard curve showing a relationship between the measurement value of the absorbance of this reference material and the known glycation amount is formed. Then, the glycation amount of Lys in Hb can be calculated by substituting the absorbance measured as described above into this standard curve.

When the sample is treated in the presence of the aforementioned acceleration compound, by using the same sample, the Hb amount can be measured accurately. Further, in accordance with this, GHbLys % can be measured accurately. In other words, first, in advance of the cleavage of Hb by protease, the acceleration compound is added to the sample containing Hb and an amount of optical change of the sample, to which the acceleration compound is added, is measured. Then, from the amount of optical change, the Hb amount in the sample is calculated. On the other hand, the glycation amount of lysine in Hb is measured by measuring the redox reaction between the glycated part and FAOD after cleaving Hb in the sample by protease. Then, the GHbLys value (GHbLys %) is preferably obtained from the Hb amount and the glycation amount of lysine. The Hb amount may be measured before or after the protease treatment.

In this example, in advance of addition of protease, the acceleration compound is added to the sample containing Hb, and an absorbance of the sample is measured. Then, the Hb amount may be obtained from the measured absorbance and the standard curve prepared in advance. In this manner, when Hb is treated with the acceleration compound, the Hb amount can be measured easily and accurately. Although the mechanism thereof is unknown, it is estimated that the structure of Hb is changed due to the acceleration compound, and unstable Hb is stabilized. For example, by measuring plural Hb-containing samples, which are the known Hb amount (known Hb concentration), by the aforementioned method, the standard curve can be formed from these measurement values and the known Hb amount (known Hb concentration). Further, the measurement wavelength of the absorbance is not limited, however is, for example, in the range of 400 to 660 nm and a treatment time of the sample with the acceleration compound is, for example, in the range of 0.2 to 30 minutes. When the Hb measurement is carried out with this method, the glycation amount (concentration) of lysine in Hb can be obtained by subsequently performing the protease treatment in the same manner as described above except that the measurement of the absorbance is performed after addition of the compound to the sample and before addition of protease. Therefore, the method of measurement can be simpler.

With respect to measurement of GHbLys %, each treatment process may be performed separately as described above. However, for example, each treatment may be performed simultaneously in combinations as described below. Further, an order of adding protease, FAOD, POD, and a chromogenic substrate is not particularly limited.

1: hemolysis treatment+protease treatment
2: protease treatment+FAOD treatment
3: FAOD treatment+POD treatment
4: protease treatment+FAOD treatment+POD treatment GHbLys is stable within the living body and collected blood.
Therefore, the timing of blood collection and the timing of measurement after blood collection are not limited at all. Within an Hb life (generally about 4 months), GHbLys is stable. Therefore, for example, the blood collection at the predetermined time defined with reference to meals and measurement of more than once, as conventional, are not necessary. The blood collection and the measurement can be performed arbitrarily. With respect to the sample after the blood collection, the measurement of GHbLys % may be performed promptly or after storage.

A method of measuring GHbLys % is not limited to such enzyme method and may be, as described above, an HPLC method, an immunization method, an electrophoresis method, a mass spectrometry method, etc. For example, first, lysine or peptide containing lysine is cleaved from Hb, and then, by the HPLC, is purified and separated into a glycation product, in which a side chain amino group of lysine is glycated, (glycated lysine or glycated lysine peptide) and a non-glycation product (lysine or lysine peptide), in which the side chain amino group of lysine is not glycated. Thereafter, quantitative analysis of this purified product may be performed by subjecting it to capillary electrophoresis and LC-MS.

Further, in these methods, for example, as described above, protease specifically cleaving lysine and lysine peptide may be used and the protease treatment may be performed in the presence of the acceleration compound. With these methods, for example, lysine or glycated lysine, or lysine peptide or glycated lysine peptide can be cleaved efficiently. Therefore, for example, the immunization method, in which cleaved glycated lysine and glycated lysine peptide are served as antigen, is effective. Further, separation can be improved by the HPLC method and the electrophoresis method. The present invention is characterized by measuring the glycation degree of the lysine residue in Hb (GHbLys %) as a postprandial hyperglycemia marker and the method of measuring GHbLys % itself is not limited at all.

<Detection of Postprandial Hyperglycemia Marker>

With respect to a method of detecting a postprandial hyperglycemia marker of the present invention, the marker is a postprandial hyperglycemia marker of the present invention, and the detection of the postprandial hyperglycemia marker is a detection of glycation of a lysine residue in Hb. The detection of glycation of lysine in Hb can be performed by measuring the postprandial hyperglycemia marker.

<Method of Determining a Risk of Diabetes>

The present invention is a method of determining a risk for a specimen to develop diabetes, and comprises the following process (a).

(a) a process of measuring a postprandial hyperglycemia marker of the present invention by measuring a glycation degree of a lysine residue in Hb by a method of measuring of the present invention with respect to a blood sample obtained from the specimen.

As described above, the inventors of the present invention found that GHbLys % shows correlation with postprandial hyperglycemia. Further, as described above, it is known that postprandial hyperglycemia is the early stage of diabetes. Therefore, with the measurement of GHbLys % in blood of patient obtained at arbitrary timing, for example, a risk for developing diabetes and the level of risk (development to the middle stage and the late stage of diabetes) can be determined. The specimen is not limited and examples thereof include human, mammals except for human, and other animals.

The method of determining a risk of the present invention preferably comprises the following process (b). Although the processes (b1) to (b5) described later are specific examples of a method of judging a risk, the present invention is not limit thereto.

(b) a process of determining a risk for the specimen to develop diabetes by at least one method selected from the group consisting of (b1) to (b5) using the glycation degree of the lysine residue in Hb measured in the process (a).

In the method (b1), a boundary value between a glycation degree of a lysine residue of Hb in blood collected from a healthy subject and a glycation degree of a lysine residue of Hb in blood collected from a postprandial hyperglycemia patient is set as an evaluation criterion. In a case where the glycation degree of the lysine residue of the specimen measured in the process (a) is relatively higher than the evaluation criterion, it is determined that the risk for developing diabetes is relatively high.

Details of this method are as follows. The boundary value serving as the evaluation criterion is set in advance. First, with respect to healthy subjects and postprandial hyperglycemic patients, blood samples are collected at arbitrary timing and GHbLys % is measured. From these results, the boundary value between the measurement value of GHbLys % of healthy subjects and the measurement value of GHbLys % of postprandial hyperglycemia patients are determined, and the thus-obtained boundary value is set as the evaluation criterion. The evaluation criterion thus obtained can be used as a general evaluation criterion. Therefore, for example, it is not necessary to set the evaluation criterion (boundary value) every time the risk with respect to the specimen is determined. On the other hand, with respect to the specimen whose risk is required to be determined, a blood sample is collected at arbitrary timing and GHbLys % is measured. Then, this measurement value is compared to the evaluation criterion. In a case where this measurement value is higher than the evaluation criterion (measurement value>boundary value), it is judged that the risk for developing diabetes is relatively high. In a case where this measurement value is lower than the evaluation criterion (measurement value<boundary value), it is judged that the risk for developing diabetes is relatively low.

Healthy subjects and postprandial hyperglycemic patients for determining the boundary value are classified by the measurement of blood glucose level according to the conventional method. An example of the method includes a method of measuring a blood glucose level of 30 minutes to 2 hours after a meal by taking 75 g of starch hydrolysate for test (for example, trade name: TRELAN-G75, manufactured by AJINOMOTO) in the fasting state (Japan Diabetes Society, "Guideline of Diabetes Diagnostic Criteria Committee in Sugar Tolerance Test").

In the method (b2), a calculation value of a glycation degree of a lysine residue of Hb, which is obtained by substituting a blood glucose level of blood collected from a specimen in the fasting state into a relational expression between a glycation degree of a lysine residue of Hb in blood collected from a healthy subject and a blood glucose level of blood collected from a healthy subject in the fasting state, is set as an evaluation criterion. In a case where the glycation degree of the lysine residue (GHbLys %) of the specimen measured in the process (a) is relatively higher than the evaluation criterion, it is determined that the risk is relatively high.

Details of this method are as follows. The evaluation criterion is set in advance. First, with respect to healthy subjects, blood samples are collected at arbitrary timing and GHbLys % is measured. Further, with respect to the healthy subjects, blood in the fasting state is collected, and the blood glucose level in the fasting state is measured. Then, a relational expression between GHbLys % of healthy subjects and a blood glucose level of healthy subjects in the fasting state is obtained. As the relational expression, a primary expression such as "GHbLys %=(a×blood glucose level in the fasting state)+b" can be used. The relational expression thus obtained can be used as a general standard expression. Therefore, for example, it is not necessary to obtain the relational expression every time the risk with respect to the specimen is determined. Next, with respect to the specimen whose risk is required to be determined, the blood glucose level in the fasting state is measured. A calculation value of GHbLys % is calculated from the blood glucose level in the fasting state of the specimen (measurement value) using the relational expression previously obtained. This calculation value of GHbLys % is defined as the evaluation criterion. On the other hand, with respect to the specimen, blood samples are collected at arbitrary timing and GHbLys % is measured. Then, this measurement value is compared to the evaluation criterion (calculation value of GHbLys %). In a case where this measurement value of GHbLys % is higher than the evaluation criterion, (measurement value>calculation value of GHbLys %), it is judged that the risk for developing diabetes is relatively high. In a case where this measurement value is lower than the evaluation criterion (measurement value<calculation value of GHbLys %), it is judged that the risk for developing diabetes is relatively low.

The blood sample used for the measurement of GHbLys % is not limited as described above and can be collected at arbitrary timing. Further, in a case where the blood glucose level in the fasting state also is measured, for example, GHbLys % may be measured using the blood sample of the fasting state.

It is preferable that the blood glucose level in the fasting state is measured, with respect to the blood sample collected 10 to 14 hours after the previous meal, by the conventionally known method. Specifically, it is general that the meal of the previous day is finished by 20:00 (or 22:00) and the blood sample is collected after 8:00 of the current day.

In the method (b3), a blood glucose level of blood collected from a specimen in the fasting state is set as an evaluation criterion. On the other hand, a calculation value of the blood glucose level of the specimen in the fasting state is obtained by substituting the glycation degree of the lysine residue of the specimen measured in the process (a) into a relational expression between a glycation degree of a lysine residue of hemoglobin in blood collected from a healthy subject and a blood glucose level of blood collected from a healthy subject in the fasting state. In a case where the calculation value of the blood glucose level of the specimen in the fasting state is relatively higher than the evaluation criterion, it is determined that the risk is relatively high.

Details of this method are as follows. The evaluation criterion is set in advance. With respect to the specimen whose risk is required to be determined, blood samples are collected in the fasting state and the blood glucose level in the fasting state is measured. This blood glucose level in the fasting state is set as the evaluation criterion. On the other hand, with respect to healthy subjects, blood samples are collected at arbitrary timing and GHbLys % is measured. Further, with respect to the healthy subjects, blood in the fasting state is collected, and the blood glucose level in the fasting state is measured. Then, a relational expression between GHbLys % of healthy subjects and a blood glucose level of healthy subjects in the fasting state is obtained. As the relational expression, the same as (b2), a primary expression such as "GHbLys %=(a×blood glucose level in the fasting state)+b" can be used. As described above, the relational expression thus obtained can be used as a general standard expression. Therefore, for example, it is not necessary to obtain the relational expression every time the risk with respect to the specimen is determined. Subsequently, with respect to the specimen whose risk is required to be determined, blood samples are collected at arbitrary timing and GHbLys % is measured. A calculation value of the blood glucose level in the fasting state is calculated from the measurement value of GHbLys % of the specimen using the relational expression previously obtained. In a case where the calculation value of the blood glucose level in the fasting state obtained from this GHbLys % of the specimen is higher than the evaluation criterion, (calculation value>measured blood glucose level in the fasting state), it is judged that the risk for developing diabetes is relatively high. In a case where the calculation value is lower than the evaluation criterion (calculation value<measured blood glucose level in the fasting state), it is judged that the risk for developing diabetes is relatively low.

The blood sample used for the measurement of GHbLys % is not limited as described above and can be collected at arbitrary timing. Further, in a case where the blood glucose level in the fasting state also is measured, for example, GHbLys % may be measured using the blood sample of the fasting state.

In the method (b4), a calculation value of a glycation degree of a lysine residue of Hb, which is obtained by substituting a glycation degree of a β chain N-terminal amino acid residue of Hb in blood collected from the specimen into a relational expression between a glycation degree of a lysine residue of Hb in blood collected from a healthy subject and a glycation degree of a β chain N-terminal amino acid residue of Hb in blood collected from a healthy subject, is set as an evaluation criterion. In a case where the glycation degree of the lysine residue (GHbLys %) of the specimen measured in the process (a) is relatively higher than the evaluation criterion, it is determined that the risk is relatively high.

Details of this method are as follows. The evaluation criterion is set in advance. First, with respect to healthy subjects, blood samples are collected at arbitrary timing and GHbLys % is measured. Further, with respect to the healthy subjects, blood samples are collected at arbitrary timing and HbA1c % is measured. Then, a relational expression between GHbLys % of healthy subjects and HbA1c % of healthy subjects is obtained. As the relational expression, a primary expression such as "GHbLys %=(a×HbA1c %)+b" can be used. The relational expression thus obtained can be used as a general standard expression. Therefore, for example, it is not necessary to obtain the relational expression every time the risk with respect to the specimen is determined. Next, with respect to the specimen whose risk is required to be determined, the blood sample is collected at arbitrary timing and HbA1c % is measured. A calculation value of GHbLys % is calculated from the measurement value of HbA1c % of the specimen using the relational expression previously obtained. This calculation value of GHbLys % is set as the evaluation criterion. On the other hand, with respect to the specimen, blood samples are collected at arbitrary timing and GHbLys % is measured. Then, this measurement value is compared to the evaluation criterion (calculation value of GHbLys). In a case where this measurement value of GHbLys % is higher than the evaluation criterion, (measurement value>calculation value of GHbLys), it is judged that the risk for developing diabetes is relatively high. In a case where this measurement value is lower than the evaluation criterion (measurement value<calculation value of GHbLys), it is judged that the risk for developing diabetes is relatively low.

The blood sample used for the measurement of GHbLys % is not limited as described above and can be collected at arbitrary timing. Further, the blood sample used for the measurement of HbA1c % is not limited and can be collected at arbitrary timing. In a case where HbA1c % and GHbLys % are measured, they can be measured using the same blood sample. A method of measuring HbA1c % is described later.

In the method (b5), a glycation degree of a β chain N-terminal amino acid residue of Hb in blood collected from a specimen is set as an evaluation criterion. On the other hand, a calculation value of the glycation degree of the β chain N-terminal amino acid residue of Hb of the specimen is obtained by substituting the glycation degree of the lysine residue of the specimen measured in the process (a) into a relational expression between a glycation degree of a lysine residue of Hb in blood collected from a healthy subject and the glycation degree of the β chain N-terminal amino acid residue of Hb. In a case where the calculation value of the glycation degree of the β chain N-terminal amino acid residue of hemoglobin is relatively higher than the evaluation criterion, it is determined that the risk is relatively high.

Details of this method are as follows. The evaluation criterion is set in advance. With respect to the specimen whose risk is required to be determined, blood samples are collected at arbitrary timing and HbA1c % is measured. This measurement value of HbA1c % is set as the evaluation criterion. On the other hand, with respect to healthy subjects, blood samples are collected at arbitrary timing and GHbLys % is measured. Further, with respect to the healthy subjects, blood samples are collected at arbitrary timing and HbA1c % is measured. Then, a relational expression between GHbLys % of healthy subjects and HbA1c % of healthy subjects is obtained. As the relational expression, as same as (b4), a primary expression such as "GHbLys %=(a×HbA1c %)+b" can be used. This relational expression can be used as a general standard expression as described above. Therefore, for example, it is not necessary to obtain the relational expression every time the risk with respect to the specimen is determined. Next, with respect to the specimen whose risk is required to be determined, the blood sample is collected at arbitrary timing, and GHbLys % is measured. A calculation value of HbA1c % is calculated from the measurement value of GHbLys % of the specimen using the relational expression previously obtained. This measurement value (HbA1c %) is compared to the evaluation criterion (calculation value of HbA1c %). In a case where this measurement value (HbA1c %) is lower than the evaluation criterion (calculation value of HbA1c %) (measurement value<calculation value of HbA1c %), it is judged that the risk for developing diabetes is relatively high. In a case where this measurement value (HbA1c %) is higher than the evaluation criterion (calculation value of HbA1c %) (measurement value>calculation value of HbA1c %), it is judged that the risk for developing diabetes is relatively low.

The blood sample used for the measurement of GHbLys % is not limited as described above and can be collected at arbitrary timing. Further, the blood sample used for the measurement of HbA1c % is not limited and can be collected at arbitrary timing. In a case where HbA1c % and GHbLys % are measured, they can be measured using the same blood sample.

Besides the aforementioned methods, for example, the risk can be judged by measuring HbA1c % and GHbLys % of a specimen, and simply calculating a difference (GHbLys %-HbA1c %) and a ratio (GHbLys %/HbA1c %) between them.

Further, in these diagnoses, for example, the greater the relative difference is, the higher the risk for developing diabetes. Specific examples of the relative difference are a difference between a calculation value of a blood glucose level in the fasting state and a measurement value of a blood glucose level in the fasting state, a difference between a calculation value of GHbLys % and a measurement value of GHbLys %, and a difference between a calculation value of HbA1c % and a measurement value of HbA1c %, and a ratio between GHbLys % and HbA1c %. In a case where these differences and the ratio are relatively high, it can be judged that the risk for developing diabetes is relatively high.

In the present invention, it is preferable that not only the measurement of GHbLys but also the measurement of HbA1c is performed together. For example, the measurement of HbA1c makes it possible, not only to judge the risk for developing diabetes of a specimen by the measurement of GHbLys, but also to judge whether a specimen is already had diabetes.

<Diagnosis of Postprandial Hyperglycemia>

The present invention is a method of diagnosing postprandial hyperglycemia of a specimen and comprises the following process (c).

(c) a process of measuring a postprandial hyperglycemia marker of the present invention by measuring a glycation degree of a lysine residue in Hb by a method of measuring of the present invention with respect to a blood sample obtained from the specimen.

As described above, the inventors of the present invention found that GHbLys % shows correlation with postprandial hyperglycemia. Therefore, with the measurement of GHbLys % in blood of a patient obtained at arbitrary timing, for example, it can be determined whether the patient has postprandial hyperglycemia.

With respect to the method of diagnosing postprandial hyperglycemia of the present invention, it is preferable that the method further comprises the following process (d). Although the processes (d1) to (d5) described later are specific examples of a judging method of postprandial hyperglycemia, the present invention is not limit thereto.

(d) a process of judging postprandial hyperglycemia of the specimen by at least one method selected from the group consisting of (d1) to (d5) using the glycation degree of the lysine residue in Hb measured in the process (c).

In the method (d1), a boundary value between a glycation degree of a lysine residue of Hb in blood collected from a healthy subject and a glycation degree of a lysine residue of Hb in blood collected from a postprandial hyperglycemia patient is set as an evaluation criterion. In a case where the glycation degree of the lysine residue of the specimen measured in the process (c) is relatively higher than the evaluation criterion, it is determined that the specimen has postprandial hyperglycemia. The method (d1) can be performed in the same manner as (b1). Specifically, in a case where the measurement value of GHbLys % of the specimen shows higher value than the evaluation criterion (measurement value>boundary value), it is judged that the possibility of postprandial hyperglycemia is relatively high. In a case where the measurement value of GHbLys % of the specimen shows lower value than the evaluation criterion (measurement value<boundary value), it is judged that the possibility of postprandial hyperglycemia is relatively low.

In the method (d2), a calculation value of a glycation degree of a lysine residue of Hb, which is obtained by substituting a blood glucose level of blood collected from a specimen in the fasting state into a relational expression between a glycation degree of a lysine residue of Hb in blood collected from a healthy subject and a blood glucose level of blood collected from a healthy subject in the fasting state, is set as an evaluation criterion. In a case where the glycation degree of the lysine residue of the specimen measured in the process (c) is relatively higher than the evaluation criterion, it is determined that the specimen has postprandial hyperglycemia. The method (d2) can be performed in the same manner as (b2). Specifically, in a case where the measurement value of GHbLys % of the specimen shows higher value than the evaluation criterion (measurement value>calculation value of GHbLys %), it is judged that the possibility of postprandial hyperglycemia is relatively high. In a case where the measurement value of GHbLys % of the specimen shows lower value than the evaluation criterion (measurement value<calculation value of GHbLys %), it is judged that the possibility of postprandial hyperglycemia is relatively low.

In the method (d3), a blood glucose level of blood collected from a specimen in the fasting state is set as an evaluation criterion. On the other hand, a calculation value of the blood glucose level of the specimen in the fasting state is obtained by substituting the glycation degree of the lysine residue of the specimen measured in the process (c) into a relational expression between a glycation degree of a lysine residue of Hb in blood collected from a healthy subject and a blood glucose level of blood collected from a healthy subject in the fasting state. In a case where the calculation value of the blood glucose level of the specimen in the fasting state is relatively higher than the evaluation criterion, it is determined that the specimen has postprandial hyperglycemia. The method (d3) can be performed in the same manner as (b3). Specifically, in a case where the calculation value of the blood glucose level of the specimen in the fasting state shows higher value than the evaluation criterion (measurement value of the blood glucose level in the fasting state) (calculation value>measurement value), it is judged that the possibility of postprandial hyperglycemia is relatively high. In a case where the calculation value of the blood glucose level of the specimen in the fasting state shows lower value than the evaluation criterion (measurement value of the blood glucose level in the fasting state) (calculation value<measurement value), it is judged that the possibility of postprandial hyperglycemia is relatively low.

In the method (d4), a calculation value of a glycation degree of a lysine residue of Hb, which is obtained by substituting a glycation degree of a B chain N-terminal amino acid residue of Hb in blood collected from a specimen into a relational expression between a glycation degree of a lysine residue of Hb in blood collected from a healthy subject and a glycation degree of a β chain N-terminal amino acid residue of Hb in blood collected from a specimen, is set as an evaluation criterion. In a case where the glycation degree of the lysine residue of the specimen measured in the process (c) is relatively higher than the evaluation criterion, it is determined that the specimen has postprandial hyperglycemia. The method (d4) can be performed in the same manner as (b4). Specifically, in a case where the measurement value of GHbLys % of the specimen shows higher value than the evaluation criterion (calculation value of GHbLys %) (measurement value >calculation value), it is judged that the possibility of postprandial hyperglycemia is relatively high. In a case where the measurement value of GHbLys % of the specimen shows lower value than the evaluation criterion (calculation value of GHbLys %) (measurement value<calculation value), it is judged that the possibility of postprandial hyperglycemia is relatively low.

In the method (d5), a glycation degree of a β chain N-terminal amino acid residue of Hb in blood collected from a specimen is set as an evaluation criterion. On the other hand, a calculation value of the glycation degree of a β chain N-terminal amino acid residue of Hb of the specimen is obtained by substituting the glycation degree of the lysine residue of the specimen measured in the process (a) into a relational expression between a glycation degree of a lysine residue of Hb in blood collected from a healthy subject and the glycation degree of the β chain N-terminal amino acid residue of Hb. In a case where the calculation value of the glycation degree of a β chain N-terminal amino acid of Hb is relatively higher than the evaluation criterion, it is determined that the risk is relatively high. The method (d5) can be performed in the same manner as (b5). Specifically, in a case where this calculation value of HbA1c % of the specimen shows higher value than the evaluation criterion (measurement value of HbA1c %) (calculation value>measurement value), it is judged that the possibility of postprandial hyperglycemia is relatively high. In a case where this calculation value of HbA1c % of the specimen shows lower value than the evaluation criterion (measurement value of HbA1c %) (calculation value<measurement value), it is judged that the possibility of postprandial hyperglycemia is relatively low.

Besides the aforementioned methods, for example, the risk can be judged by measuring HbA1c % and GHbLys % of a specimen, and simply calculating a difference (GHbLys %-HbA1c %) and a ratio (GHbLys %/HbA1c %) between them.

Further, in these diagnoses, for example, the greater the relative difference is, the higher the level of postprandial hyperglycemia. Specific examples of the relative difference are a difference between a calculation value of a blood glucose level in the fasting state and a measurement value of a blood glucose level in the fasting state, a difference between a calculation value of GHbLys % and a measurement value of GHbLys %, and a difference between a calculation value of HbA1c % and a measurement value of HbA1c %, a ratio between GHbLys % and HbA1c %. In a case where these differences and the ratio are relatively high, it can be judged that the level of postprandial hyperglycemia is relatively high.

In the present invention, it is preferable that not only the measurement of GHbLys but also the measurement of HbA1c is performed. For example, the measurement of HbA1c makes it possible, not only to judge postprandial hyperglycemia of a specimen by the measurement of GHbLys, but also to judge whether a specimen already had diabetes.

<Method of Measuring HbA1c %>

The method of measuring HbA1c % is not limited and conventionally known methods (an enzymatic method, an HPLC method, an immunization method, an electrophoresis method, a mass spectrometry method, etc.) can be adopted. As an example, the method of measuring by the enzymatic method is explained.

The method of measuring HbA1c % by the enzymatic method can be performed in the same manner as the method of measuring GHbLys % except that Hb is treated with protease, a β chain N-terminal valine or peptide containing a β chain N-terminal valine (terminal peptide) is cleaved, and the FAOD acts on a glycated part of an α-amino group of valine.

Protease is not particularly limited, however the protease as described above can be used. Particularly, protease that acts specifically on the δ-chain N-terminal and catalyzes the cleavage of the N-terminal peptide (for example, JP 2000-300294 A and JP 2004-344052 A) is preferably used. Further, examples of protease that catalyzes the cleavage of the β chain N-terminal valine include protease disclosed in WO 2000/50579 A (Japanese Patent No. 3668801), WO 2000/61732 A, JP 2002-315600 A and the like.

FAOD used for the method of measuring HbA1c is not particularly limited, but is preferably an enzyme that catalyzes a reaction in which an α-amino group acts on the glycated amino acid or the glycated peptide so as to generate hydrogen peroxide and α-keto aldehyde (hereinafter, referred to as "FAOD-α").

Specific examples of such FAOD-α include FPDX-CE (trade name) manufactured by KIKKOMAN Corporation, FPDX-EE (trade name) manufactured by KIKKOMAN Corporation, fructosyl amine oxidase disclosed in WO2004/029251, fructosyl amine oxidase disclosed in JP2004-275013A and JP2004-275063A, and FAOD derived from *penicillium* (JPH8-336386A).

When fructosyl Val-His is cleaved from, for example, an Hb β chain N-terminal by the protease treatment, because of this FAOD treatment, sugar bonded to an α-amino group of Val is isolated and α-keto aldehyde (sugar residue), Val-His, and hydrogen peroxide are generated.

Further, for example, the HbA1c value can be calculated with the following Formula. The HbA1c value is a glycation degree of a β chain N-terminal valine of Hb and is referred to as HbA1c %.

$$HbA1c\% = (HbA1c/\text{total } Hb) \times 100$$

In the Formula, HbA1c includes a glycation amount of a β chain N-terminal valine of Hb (or glycation concentration). Total Hb includes a total Hb amount (or Hb concentration), a total HbA amount (or HbA concentration), or an amount of a β chain N-terminal valine of Hb (including glycated valine). On the basis of the aforementioned Formula, HbA1c % can be obtained by calculating a ratio (percent) between a glycation amount of a β chain N-terminal valine of Hb (HbA1c concentration) and a total Hb amount in a sample (Hb concentration).

Calculation of the glycation amount can be performed by measuring a level of developed color of a chromogenic substrate. Specifically, for example, the calculation of the glycation amount can be performed using a standard curve obtained by plotting a relationship between the known glycation amount of a β chain N-terminal of Hb and the absorbance. For example, with respect to Hb reference material whose glycation amount of the β chain N-terminal is known, the absorbance measurement is performed in the same manner as described above, and a standard curve showing a relationship between the measurement value of the absorbance of this reference solution and the known glycation amount is formed. Then, the absorbance measured as described above is substituted into this standard curve, and thereby calculating the glycation amount of the β chain N-terminal.

(Measurement of HbA1c and GHbLys)

HbA1c and GHbLys can be measured continuously with the same sample by using a substrate specificity of FAOD. In other words, a sample containing Hb is treated with protease and a β chain N-terminal valine or a β chain N-terminal peptide, and lysine or peptide containing lysine are cleaved. Then, first, HbA1c is measured by treating the sample with FAOD-α that specifically acts on a glycated part of an α-amino group (for example, a glycated part of valine) and hardly acts on a glycated part of an amino acid side chain. Thereafter, further, GHbLys is measured by treating the sample with FAOD-S that specifically acts on a glycated part of a lysine side chain and hardly acts on a glycated part of an α-amino group. However, a treatment order of FAOD is not limited thereto. For example, HbA1c may be measured by treating the sample with FAOD-α after measuring GHbLys by treating the sample with FAOD-S.

Further, in a case where a glycation degree of Hb in hemocyte is measured using a whole blood sample, use of the aforementioned acceleration compound makes it possible to obtain the following further advantages. When a glycation degree of protein in hemocyte is measured, normally, a whole blood sample is applied with a hemolysis treatment and is used as a hemolysis sample. In this state, in the hemolysis sample, glycated protein (for example, glycated albumin) in serum is present. However, when the protease treatment is performed in the presence of the acceleration compound, although cleavage of the aforementioned glycated Hb is accelerated, cleavage of glycated albumin is inhibited, although the mechanism is unknown. Therefore, for example, the problem, in which glycated albumin or the like is mixed in the sample and FAOD also acts on the glycated part thereof, can be avoided and a measurement accuracy can further be improved. Such problem occurs in a condition where protease acts on both Hb and albumin and FAOD added later acts on the cleavage products of both proteins. Therefore, this problem can be solved by selecting a protease that selectively cleaves a target part of a target protein (glycated amino acid and glycated peptide on which FAOD is acted).

<Method of Measuring Average Blood Glucose Level>

A method of measuring an average blood glucose level of the present invention is a method of measuring an average blood glucose level reflecting a postprandial blood glucose level and comprises the following processes (x) and (y).

(x) a process of measuring an average blood glucose level marker measuring a glycation degree of a lysine residue in Hb according to a method of measuring a postprandial hyperglycemia marker of the present invention, the average blood glucose level marker being the postprandial hyperglycemia marker of the present invention; and (y) a process of calculating the average blood glucose level reflecting a postprandial blood glucose level by substituting the glycation degree of the lysine residue in Hb measured in the process (x) to a relational expression between a glycation degree of a lysine residue in Hb and an average blood glucose level reflecting a postprandial blood glucose level.

As described above, HbA1c is an indicator of a usual average value of blood glucose level in past and is not an indicator of an average blood glucose level that reflects intraday changes. In contrast, the marker of the present invention can be an indicator of an average blood glucose level reflecting a postprandial blood glucose level. Therefore, measurement of the average blood glucose marker (postprandial hyperglycemia marker) of the present invention makes it possible to calculate the average blood glucose marker that reflects a postprandial blood glucose level. Further, in a case where this calculated average blood glucose level is relatively higher than an average blood glucose level of a healthy subject, it can be judged that there is a possibility of postprandial hyperglycemia. Further, when the measurement of HbA1c is also performed, further excellent judgment results can be obtained.

The relational expression is not particularly limited. For example, the relational expression can be formed as follows. Blood is collected from plural patients each having different postprandial blood glucose level, and GHbLys % is measured. In contrast, from the same plural patients, blood is collected for several times at predetermined timings including after a meal, and blood glucose level with respect to each blood sample is measured. The blood glucose level of each patient is totaled and an average value of each patient is calculated. This average value is an average blood glucose level that reflects a blood glucose level after a meal. Examples of the timing of blood collection of samples for measuring a blood glucose level include fasting state in the early morning, before bedtime, right before a meal, right after a meal, 30 minutes after a meal, 1 hour after a meal, and two hours after a meal. Then, with respect to each patient, a standard curve can be formed by plotting GHbLys % and an average blood glucose level that reflects a postprandial blood glucose level.

<Kit>

A kit for measuring a marker of the present invention is a kit used for a method of measuring a postprandial hyperglycemia marker of the present invention and comprises protease, FAOD, POD, and a substrate developing a color by oxidation. Use of this kit makes it possible to simply and easily perform the method of measuring the postprandial hyperglycemia marker of the present invention. The structural components as in the above can be used as structural components of the kit of the present invention. Further, the kit of the present invention suitably may contain the aforementioned substance that can be used in measurement of the postprandial hyperglycemia marker of the present invention. Examples of the substance include the acceleration compound, a tetrazolium compound, etc.

A kit for determining a risk of the present invention is a kit used for a method of determining a risk of developing diabetes of the present invention and comprises protease, FAOD, POD, and a substrate developing a color by oxidation. Further, a kit for diagnosing postprandial hyperglycemia of the present invention is a kit used for a method of diagnosing postprandial hyperglycemia of the present invention and comprises protease, FAOD, POD, and a substrate developing a color by oxidation. Structures of these kits may be the same as the kit for measuring the marker of the present invention.

Hereinafter, the present invention is explained in detail with Examples and Comparative Examples. However, the present invention is not limited thereto.

Example 1

The day before an examination, a glucose solution with a predetermined concentration was prepared by dissolving glucose into 0.85% by weight of normal saline. The concentrations were, 500 mM, 900 mM, 1900 mM, and 3500 mM. As for blank (BLK), 0.85% by weight of normal saline was used (glucose concentration 0 mM).

Blood of a healthy subject was collected in a heparin Na tube and separated into plasma and hemocyte by a centrifugal separation. 3 mL of the separated hemocyte was collected in a screw tube (13.5 ml). Further, 2.7 ml of the separated plasma and 0.3 mL of the normal saline (blank) or 0.3 mL of each glucose solution were mixed respectively to prepare glucose added blood. A glucose concentration in glucose added blood was 0 mM, 50 mM, 90 mM, 190 mM, and 350 mM, respectively. These glucose added blood was kept warm in an incubator of 37° C. while mixing it with a wave loader. Then, a predetermined time (3 hours, 6 hours, and 24 hours) after the start of warming, they were collected by 1.25 ml. The collected glucose added blood was separated into hemocyte and plasma by a centrifugal separation, and the thus-obtained plasma was defined as a measurement sample of glycated albumin and glucose concentration. On the other hand, 0.6 ml of hemocyte was collected from the separated hemocyte. Then, about tenfold volume of a 1.3% (w/v) salt solution was added thereto, and hemocyte was mixed with inversion at room temperature for 10 minutes and washed. Thereafter, it was separated into hemocyte and supernatant by a centrifugal separation, and then supernatant was removed. The hemocyte thus obtained was washed with the aforementioned salt solution again, and collected hemocyte was defined as a measurement sample of glycated Hb.

Measurements of HbA1c and unstable HbA1c were performed by directly using the hemocyte sample with an ADAMS-Ale HA-8160 (manufactured by ARKRAY INC.) which is an HPLC method.

On the other hand, with respect to measurement of GHbLys, a hemolysis sample, which is prepared by diluting the aforementioned hemocyte sample to 51 fold (volume) with the following hemolysis reagent, was used. 20 μL of the aforementioned hemolysis sample and 76 μL of the following protease reagent were mixed and incubated at 37° C. for 5 minutes. Further, 19 μL of the following chromogenic reagent was added and incubated at 37° C. for 3 minutes. An amount of increase in absorbance in 3 minutes was measured (wavelength of 751 nm and 571 nm). For the measurement of the absorbance, an autoanalyzer (trade name: JCA-BM8, manufactured by JEOL) was used. The absorbance at the wavelength of 751 nm indicates a GHbLys concentration and the absorbance at the wavelength of 571 nm indicates an Hb concentration.

TABLE 1

| (Hemolysis reagent: pH 9.4) | |
|---|---|
| CHES | 80 mmol/L |
| MOPS | 80 mmol/L |
| Polyoxyethylene laurylether | 9 g/L |
| (Protease reagent: pH 5.5) | |
| WST-3 (manufactured by DOJINDO LABORATORIES) | 2 mmol/L |
| $NaN_3$ | 0.6 mmol/L |
| NaCl | 100 mmol/L |
| $CaCl_2$ | 2 mmol/L |
| Neutral protease (manufactured by ARKRAY INC.) | 4 MU/L |
| MES | 1 mmol/L |
| (Chromogenic reagent: pH 7) | |
| DA-64 (manufactured by Wako Pure Chemical Industries, Ltd.) | 80 μmol/L |
| FAODL (manufactured by ARKRAY INC.)* | 36 KU/L |
| Tris-HCl | 380 mmol/L |
| $NaN_3$ | 0.5 mmol/L |

*FAOD derived from gibberella (FAOD-αS)

A GHbLys concentration and a Hb concentration were obtained by substituting each measured absorbance into a previously formed standard curve that shows a relationship between an Hb concentration (g/L) or a GHbLys concentration (g/L) and an absorbance. Then, GHbLys % was calculated with the following formula. The standard curve was formed by plotting the absorbance and the Hb concentration (g/L) or the GHbLys concentration (g/L) with respect to a specimen group whose Hb concentration (g/L) and GHbLys concentration (g/L) are known.

$GHbLys(\%) = (GHbLys$ concentration/$Hb$ concentration$) \times 100$

For measurement of glucose, a measurement kit, LiqTec Glu HK (trade name) manufactured by Roche Diagnostics GMBH, was used. Glucose was measured on the basis of an analytical parameter and instruction provided from the manufacturer. For the measurement of absorbance, the aforementioned autoanalyzer was used.

Figure 2:
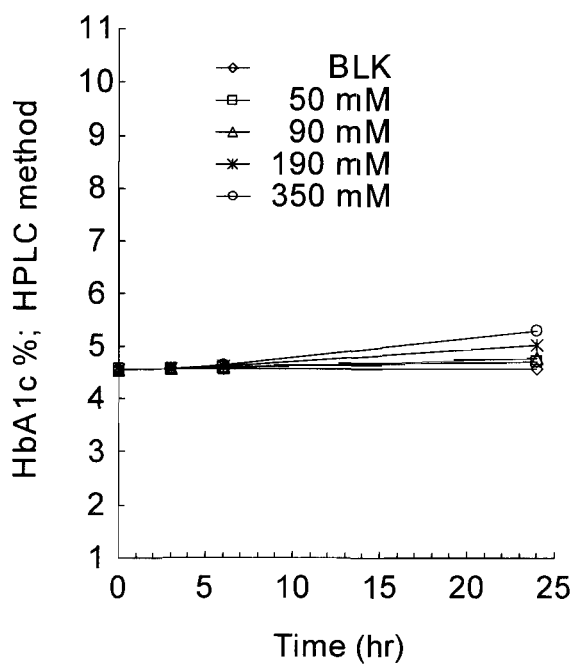
FIG. 2 is a graph showing a relationship between an incubation time of glucose added blood and hemocyte HbA1c % in Example 1 of the present invention.
Figure 3:
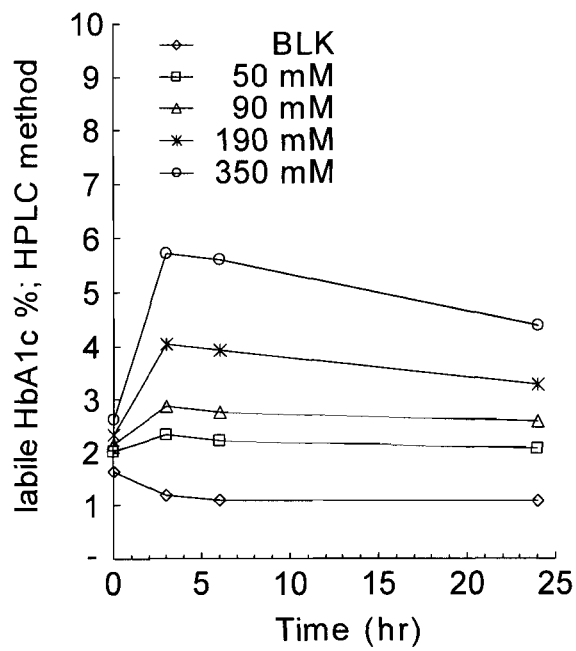
FIG. 3 is a graph showing a relationship between an incubation time of glucose added blood and hemocyte unstable HbA1c % in Example 1 of the present invention.
Figure 4:
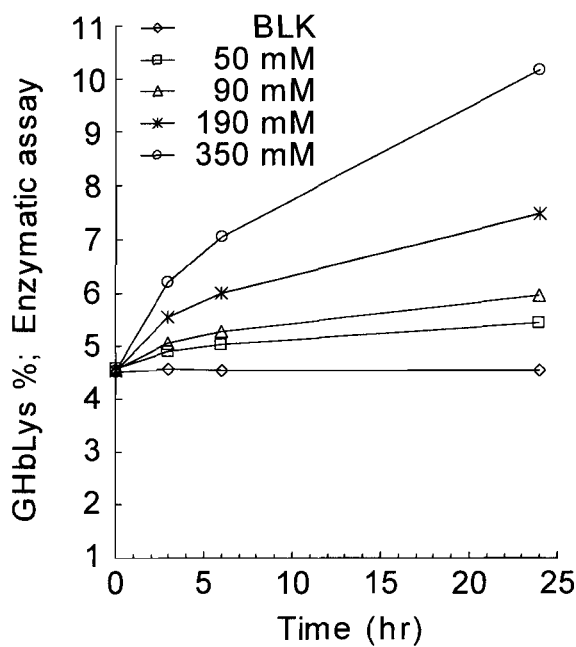
FIG. 4 is a graph showing a relationship between an incubation time of glucose added blood and hemocyte GHbLys % in Example 1 of the present invention.

These results are shown in FIGS. 1 to 4. FIG. 1 is a graph showing a relationship between an incubation time of glucose added blood and a plasma glucose concentration. FIG. 2 is a graph showing a relationship between an incubation time of glucose added blood and hemocyte HbA1c %. FIG. 3 is a graph showing a relationship between an incubation time of glucose added blood and hemocyte unstable HbA1c %. FIG. 4 is a graph showing a relationship between an incubation time of glucose added blood and hemocyte GHbLys %.

FIG. 1 shows changes in plasma glucose concentration. As shown in FIG. 1, although the glucose concentration is decreased over time because the hemocyte cell digests glucose, glucose residue was confirmed even with a sample 24 hours after the start of incubation. FIG. 2 shows changes in stable HbA1c % of hemocyte. As shown in FIG. 2, with respect to the stable HbA1c %, the measurement value was not increased even 6 hours after the start of incubation with glucose. Further, even in a case where a glucose concentration was 350 mM, the measurement value of 24 hours later was increased only by about 0.8%. This is because, as described above, unstable HbA1c hardly changes to stable HbA1c.

Next, FIG. 3 shows changes in unstable HbA1c % of hemocyte. Although the unstable HbA1c % was changed in accordance with a glucose concentration added to a sample, when a glucose concentration in plasma is decreased as shown in FIG. 1, it was decreased in accordance therewith. This is because the generation of unstable HbA1c has a balanced relation with a glucose concentration and it becomes Hb again in accordance with decrease of glucose. In contrast, as shown in FIG. 4, GHbLys of hemocyte showed the following behavior. That is, as shown in FIG. 4, GHbLys % was changed in accordance with a glucose concentration added to a sample and generation thereof was confirmed even with a brief incubation of 3 hours. Further, a measurement value of GHbLys % was increased in response to an incubation time. That is, unlike stable HbA1c and unstable HbA1c, GHbLys is a glycated protein generated even with a brief increase of blood glucose level, and it can be said that the measurement value thereof is an indicator sensitively in response to the brief increase of blood glucose level.

With respect to a measurement sample (BLK) to which glucose is not added, the measurement was performed again 14 days after preparation of the sample. As a result, a glucose concentration was 0 and there were no changes in HbA1c % and GHbLys %. Accordingly, it was confirmed that a generated glycation product existed without degradation. Therefore, it is obvious that these values depend on an Hb life and a glucose concentration only.

From the aforementioned results, even with postprandial hyperglycemia whose blood glucose level is increased only in a short time after a meal, it was found that a blood glucose level could indirectly be detected by measuring GHbLys.

Example 2

Blood of a healthy subject was collected with a blood collecting tube containing heparin lithium. This blood was separated into a hemocyte fraction and a plasma fraction by leaving it at room temperature for 2 hours to precipitate hemocyte. Then, glucose added plasma was prepared by adding and dissolving 100 mg of glucose into 0.5 mL of separated plasma and leaving it at room temperature for 3 hours. Thereafter, the separated hemocyte and plasma (glucose non-added plasma and glucose added plasma) were mixed at the following ratio, stirred gently, and kept warm at 37° C. With respect to samples of 0 minute after, 30 minutes after, 1 hour after, 2 hours after, and 3.5 hours after the start of mixing, HbA1c % and GHbLys % were measured with the following method.

TABLE 2

| | Sample 1 | Sample 2 | Sample 3 | Sample 4 |
|---|---|---|---|---|
| Hemocyte | 0.3 mL | 0.3 mL | 0.3 mL | 0.3 mL |
| Glc non-added plasma | 0.3 mL | 0.2 mL | 0.1 mL | — |
| Glc added plasma | — | 0.1 mL | 0.2 mL | 0.3 mL |
| Glc concentration (mmol/L) | 0 | 180 | 360 | 540 |

<Method of Measuring HbA1c %>

0.065 mL of the sample and 0.065 mL of purified water were mixed, 0.078 mL of reagent R1 of the following composition was added thereto, and it was incubated at 37° C. for 5 minutes. In this state, with respect to this reaction solution, a first absorbance measurement ($A_1$) at 658 nm and a first absorbance measurement ($B_1$) at 571 nm were performed. Next, 0.0185 mL of reagent R2 of the following composition was added to the aforementioned solution and incubated at 37° C. for 5 minutes. In this state, with respect to this reaction solution, an absorbance measurement ($A_2$) at 658 nm was performed. Then, an absorbance corresponding to an HbA1c concentration (glycation concentration of a β chain N-terminal valine of Hb) was calculated. This calculation was made by multiplying the second absorbance ($A_2$) by a value that corrects capacitance change (0.081/0.1095) and substracting the first absorbance ($A_1$) from the thus-obtained value. This calculated value was defined as an HbA1c absorbance. The first absorbance ($B_1$) at 571 nm corresponds to an Hb concentration in the sample. Next, from previously prepared standard curves, an HbA1c concentration and an Hb concentration were calculated with respect to each sample. The standard curves were a standard curve showing a relationship between an HbA1c concentration and an absorbance and a standard curve showing a relationship between an Hb concentration and an absorbance. Then, HbA1c % was obtained by dividing the calculated value of HbA1c concentration by the calculated value of Hb concentration and centupling it. The standard curve was formed, using reference material whose HbA1c concentration and Hb concentration were known, by measuring absorbance in the same manner as described above and plotting a relationship between each concentration and absorbance. For the measurements of absorbance, an autoanalyzer, BM-8 manufactured by JEOL, was used.

TABLE 3

| (R1: pH 7) | |
|---|---|
| FPOX-CE (manufactured by KIKKOMAN Corporation) | 1.5 KU/L |
| POD | 10 KU/L |
| $KNO_2$ | 4 mmol/L |
| Dodecyl maltoside | 2.5 g/L |
| PIPES buffer | 30 mmol/L |
| (R2: pH 5.5) | |
| Metalloprotease (manufactured by Arkray, Inc.) | 1800 KU/L |
| DA-67 (manufactured by Wako Pure Chemical Industries, Ltd.) | 0.03 mmol/L |
| Hexadecyltrimethylammonium | 0.1 g/L |
| $CaCl_2$ | 5 mmol/L |
| Tris buffer | 200 mmol/L |

<Method of Measuring GHbLys %>

0.065 mL of the sample and 0.065 mL of purified water were mixed, 0.078 mL of reagent R1 of the following composition was added thereto, and it was incubated at 37° C. for 5 minutes. In this state, with respect to this reaction solution, a first absorbance measurement ($A_1'$) at 658 nm and a first absorbance measurement ($B_1'$) at 571 nm were performed. Next, 0.0185 mL of reagent R2 of the following composition was added to the aforementioned solution and incubated at 37° C. for 5 minutes. In this state, with respect to this reaction solution, an absorbance measurement ($A_2'$) at 658 nm was performed. Then, an absorbance corresponding to a GHbLys concentration (glycation concentration of a lysine side chain of Hb) was calculated. This calculation was made by multiplying the second absorbance ($A_2'$) by a value that corrects capacitance change (0.081/0.1095) and substracting the first absorbance ($A_1'$) from the thus-obtained value. This calculated value was defined as a GHbLys absorbance. The first absorbance ($B_1'$) at 571 nm corresponds to an Hb concentration in the sample. Next, from previously prepared standard curves, a GHbLys concentration and an Hb concentration were calculated with respect to each sample. The standard curves were a standard curve showing a relationship between a GHbLys concentration and an absorbance and a standard curve showing a relationship between an Hb concentration and an absorbance. Then, GHbLys % was obtained by dividing the calculated value of GHbLys concentration by the calculated value of Hb concentration and centupling it. The standard curve was formed, using reference material whose GHbLys concentration and Hb concentration were known, by measuring absorbance in the same manner as described above and plotting a relationship between each concentration and absorbance. For the measurements of absorbance, an autoanalyzer, BM-8 manufactured by JEOL, was used.

TABLE 4

| (R1: pH 7) | |
|---|---|
| FAODL (manufactured by Arkray, Inc.)* | 5 KU/L |
| POD | 10 KU/L |
| $KNO_2$ | 4 mmol/L |
| Dodecyl maltoside | 2.5 g/L |
| PIPES buffer | 30 mmol/L |
| (R2: pH 5.5) | |
| Metalloprotease (manufactured by Arkray, Inc.) | 1800 KU/L |
| DA-67 (manufactured by Wako Pure Chemical Industries, Ltd.) | 0.03 mmol/L |
| Hexadecyltrimethylammonium | 0.1 g/L |
| $CaCl_2$ | 5 mmol/L |
| Tris buffer | 200 mmol/L |

*FAOD derived from gibberella (FAOD-αS)

Figure 5:
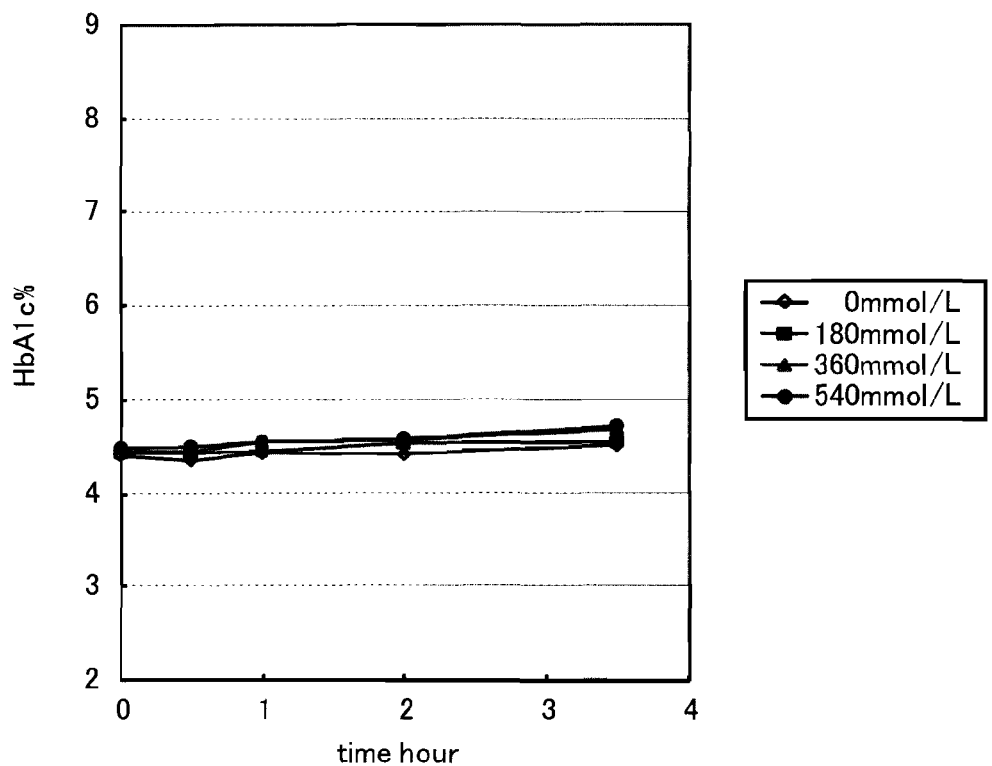
FIG. 5 is a graph showing a relationship between HbA1c % and an incubation time with glucose in Example 2 of the present invention.
Figure 6:
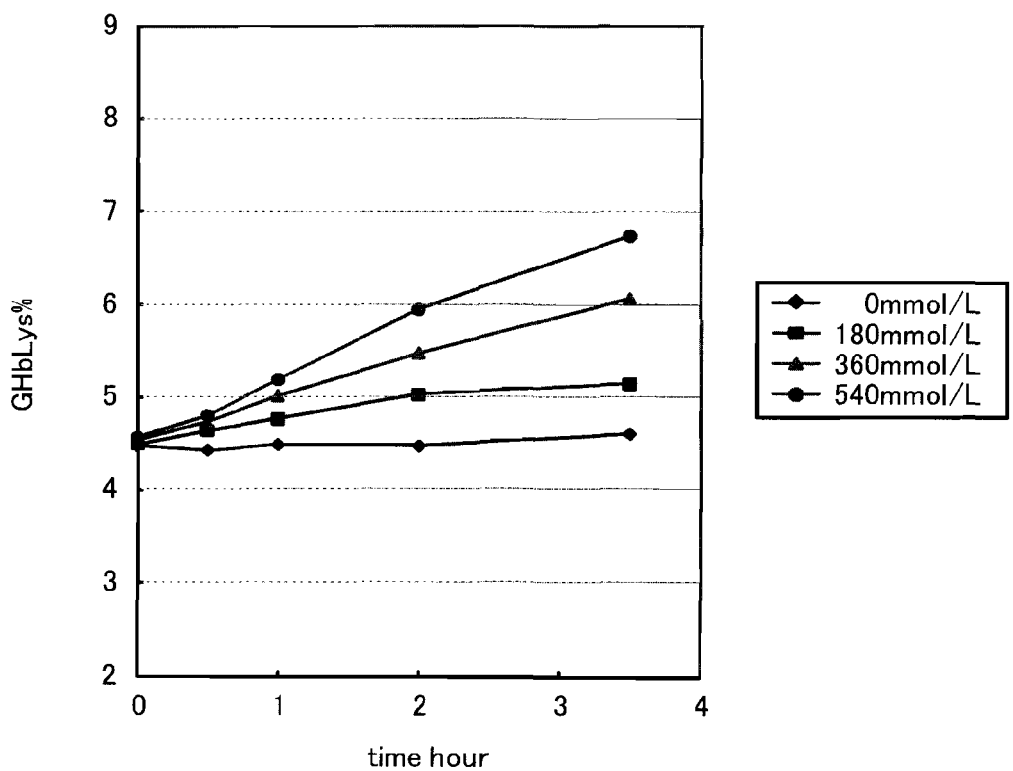
FIG. 6 is a graph showing a relationship between GHbLys % and an incubation time with glucose in Example 2 of the present invention.

These results are shown in FIGS. 5 and 6. FIG. 5 is a graph showing a relationship between HbA1c % of each sample and an incubation time with glucose of each sample. FIG. 6 is a graph showing a relationship between GHbLys % of each sample and an incubation time with glucose of each sample.

In FIGS. 5 and 6, ◇◆ indicate a sample 1 whose glucose concentration is 0 mmol/L, ■ indicates a sample 2 whose glucose concentration is 180 mmol/L, ▲ indicates a sample 3 whose glucose concentration is 360 mmol/L, and ● indicates a sample 4 whose glucose concentration is 540 mmol/L. As shown in FIG. 5, even with respect to samples having different glucose concentration of 0 mmol/L to 540 mmol/L, HbA1c % among samples were rarely changed. Further, with respect to samples having same glucose concentration, even in a case where an incubation time with glucose was changed from 0 to 3.5 hours, HbA1c % among samples were rarely changed. From these results, it is found that, within a range of 0 to 3.5 hours incubation time with glucose, regardless of a glucose concentration of a sample, HbA1c rarely is generated. In contrast, as shown in FIG. 6, a measurement value of GHbLys % is increased in accordance with an increase in a glucose concentration of a sample. Further, a measurement value of GHbLys % is increased also in accordance with an increase in an incubation time with glucose. From these results, it is found that generation of GHbLys is dependent on a glucose concentration in a sample and an incubation time.

Further, from these results, as described below, it was proved that postprandial hyperglycemia and diabetes can be distinguished when HbA1c % is measured together with GHbLys %. As shown in FIG. 5, with a brief incubation time with glucose, HbA1c is not increased. On the other hand, in a case such as diabetes, in which a glucose level is high even in the fasting state, since contact time of Hb with glucose is increased, HbA1c is generated. Therefore, HbA1c serves not as an indicator of postprandial hyperglycemia but as an indicator of diabetes. In contrast, GHbLys is generated in a case of postprandial hyperglycemia. Therefore, when both GHbLys % and HbA1c % are measured, it can be judged whether one is postprandial hyperglycemia by the measurement of GHbLys % and it can be judged if it is already developed to diabetes by the measurement of HbA1c %.

Example 3

Whole blood was collected from a diabetes patient and a healthy subject in the same manner as Example 2. These whole blood were stored in a refrigerator (0 to 25 days) after leaving them at room temperature for a day. After gently stirring the stored whole blood, 0.5 mL of purified water was added to 0.02 mL of whole blood to hemolyze. Using this hemolysis sample, GHbLys % was measured in the same manner as Example 2.

Figure 7:
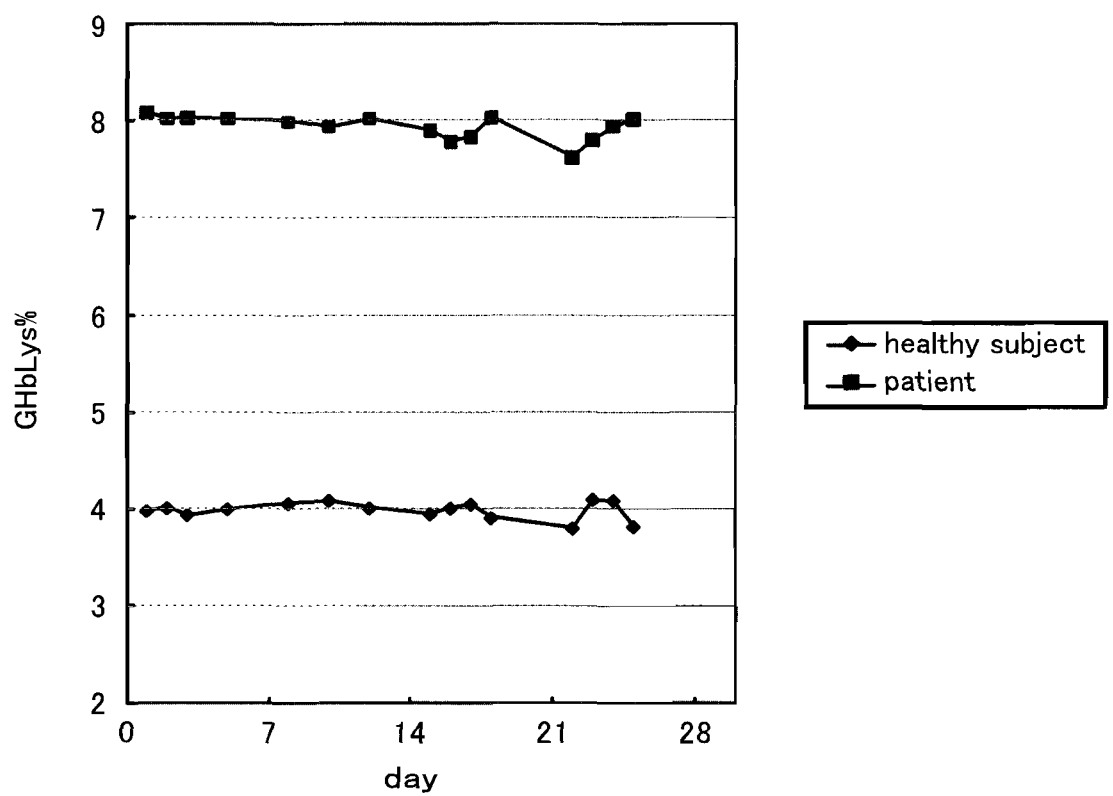
FIG. 7 is a graph showing a relationship between a storage time of whole blood and GHbLys % in Example 3 of the present invention.

These results are shown in FIG. 7. FIG. 7 is a graph showing a relationship between a storage time of whole blood and GHbLys %. In FIG. 7, ♦ indicates a result of a sample of a healthy subject and ■ indicats a result of a sample of a diabetes patient.

As shown in FIG. 7, a measurement value of GHbLys % was rarely changed even in a case where each whole blood was left from 0 to 25 days. From this, it is found that GHbLys % is rarely changed in blood in a living body of a specimen and in blood collected from a specimen. In other words, unlike a method of directly measuring a blood glucose level as conventional, according to the measurement of GHbLys %, for example, a timing of blood collection, a time for analyzing the collected blood, etc. are not limited at all. Therefore, effort of patients and medical institutions can be reduced.

Example 4

Although diabetes patients indicate constant hyperglycemia, a method of controlling thereof varies depending on type 1 patients and type 2 patients. First, since type 1 patients cannot generate insulin in the body, insulin is injected from outside. Due to this insulin injected before a meal, blood glucose is decreased promptly. However, since the living body does not secrete an amount of insulin corresponding to blood glucose, postprandial hyperglycemia occurs due to temporary insulin shortages, and then a blood glucose level is decreased. Therefore, with respect to type 1 patients, due to administration of insulin, HbA1c % representing a usual average value of blood glucose level shows a value lower than a state where insulin is not administered. However, GHbLys % serving as an indicator of postprandial hyperglycemia shows still a high value. In contrast, since type 2 patients can generate a certain amount of insulin corresponding to blood glucose in the body, blood glucose thereof changes gradually. Therefore, even though insulin is not administered, type 2 patients show lower HbA1c %, that represents a usual average value of blood glucose level, as compared to type 1 patients to whom insulin is not administered. Because of the use of insulin and retardant, which delays absorption of sugar in the small intestine, postprandial hyperglycemia hardly occurs. Therefore, it is considered that, due to administration of retardant, GHbLys % serving as an indicator of postprandial hyperglycemia shows a value lower than a state where a sugar absorption retardant is not administered. Therefore, GHbLys % was measured by administering insulin to type 1 patients (sugar absorption retardant is not administered) and administering insulin and sugar absorption retardant to type 2 patients. Accordingly, a relationship between GHbLys % showing postprandial hyperglycemia and HbA1c % showing a usual average value of blood glucose level was confirmed.

27 diabetes patients were divided into type 1 patients to whom only insulin is administered and type 2 patients to whom insulin and sugar absorption retardant are administered. Then HbA1c % and GHbLys % of each patient were measured. HbA1c % was measured using a commercially available measuring instrument (trade name: ADAMS-A1c HA-8160, manufactured by ARKRAY INC.) according to instruction thereof. GHbLys % was measured in the same manner as Example 2. Results of HbA1c %, GHbLys %, and a difference therebetween (GHbLys %-HbA1c %) are shown in the following table.

TABLE 5

| <type 1 patient> | | | <type 2 patient> | | |
|---|---|---|---|---|---|
| GHbLys % | HbA1c % | GHbLys % – HbA1c % | GHbLys % | HbA1c % | GHbLys % – HbA1c % |
| 6.64 | 6.53 | 0.11 | 6.82 | 7.19 | −0.37 |
| 6.55 | 6.03 | 0.52 | 6.95 | 7.20 | −0.25 |
| 6.23 | 5.95 | 0.28 | 6.39 | 6.65 | −0.26 |
| 5.40 | 5.21 | 0.19 | 7.20 | 7.52 | −0.32 |
| 7.23 | 7.08 | 0.15 | 7.52 | 7.96 | −0.44 |
| 10.91 | 10.17 | 0.74 | 6.39 | 6.60 | −0.21 |
| 8.86 | 8.09 | 0.77 | 7.13 | 7.17 | −0.04 |
| 8.38 | 8.23 | 0.15 | 6.01 | 6.32 | −0.31 |
| 10.99 | 9.38 | 1.61 | 7.23 | 7.50 | −0.27 |
| 7.80 | 7.62 | 0.18 | 5.64 | 5.96 | −0.32 |
| 7.74 | 7.56 | 0.18 | 6.05 | 6.24 | −0.19 |
| 5.90 | 5.72 | 0.18 | 6.33 | 6.70 | −0.37 |
| 8.49 | 8.43 | 0.06 | | | |
| 9.64 | 8.75 | 0.89 | | | |

As shown in Table 5, with respect to type 1 patients to whom insulin is administered, measured values of GHbLys % were larger than that of HbA1c %. With respect to type 2 patients to whom sugar absorption retardant is administered, measured values of GHbLys % were smaller than that of HbA1c %. As described above, type 1 patients to whom insulin is administered often show postprandial hyperglycemia and type 2 patients to whom insulin and sugar absorption retardant are administered rarely show postprandial hyperglycemia. Therefore, as shown in Table 5, with respect to type 1 patients, GHbLys % indicating postprandial hyperglycemia showed larger values than HbA1c % and "GHbLys %-HbA1c %" showed larger values than that of type 2 patients. This result supports the fact that GHbLys % reflects a blood glucose level after a meal. Further, from these results, it was found that postprandial hyperglycemia (borderline diabetes) can be judged not only by the detection of GHbLys % but also by the relationship between GHbLys % and HbA1c %.

INDUSTRIAL APPLICABILITY

As described above, according to the present invention, postprandial hyperglycemia can indirectly be detected by measuring GHbLys. Postprandial hyperglycemia is so-called borderline diabetes, and the sufficient prevention at this stage allows delay and prevention of development of diabetes as well as suppression of complications. Therefore, the present invention is very effective as a method of diagnosing postprandial hyperglycemia.

The invention claimed is:

1. A method of determining a risk for a specimen to develop diabetes, wherein the method of determining a risk comprises following process (a) and (b):
   (a1) a process of measuring a postprandial hyperglycemia marker, wherein the postprandial hyperglycemia marker comprises hemoglobin having a glycated lysine residue, by measuring a glycation degree of a lysine residue of hemoglobin by a method comprising a step of at least one selected from the group consisting of applying a high-performance liquid chromatography method, an immunization method, an enzymatic method and an electrophoresis method with respect to a blood sample obtained from the specimen;
(a2) a process of determining a risk for the specimen based on the postprandial hyperglycemia marker measured by the step (a1); and
(b) a process of determining a risk for the specimen to develop diabetes by at least one method selected from the group consisting of (b1) to (b5) using the glycation degree of the lysine residue of hemoglobin measured in the process (a):
(b1) setting a boundary value between a glycation degree of a lysine residue of hemoglobin in blood collected from a healthy subject and a glycation degree of a lysine residue of hemoglobin in blood collected from a postprandial hyperglycemia patient as an evaluation criterion, and determining the risk for developing diabetes being relatively high in a case where the glycation degree of the lysine residue of the specimen measured in the process (a) is relatively higher than the evaluation criterion;
(b2) setting a calculation value of a glycation degree of a lysine residue of hemoglobin, which is obtained by substituting a blood glucose level of blood collected from the specimen in the fasting state into a relational expression between a glycation degree of a lysine residue of hemoglobin in blood collected from a healthy subject and a blood glucose level of blood collected from a healthy subject in the fasting state, as an evaluation criterion, and determining the risk for developing diabetes being relatively high in a case where the glycation degree of the lysine residue of the specimen measured in the process (a) is relatively higher than the evaluation criterion;
(b3) setting a blood glucose level of blood collected from the specimen in the fasting state as an evaluation criterion, on the other hand, obtaining a calculation value of the blood glucose level of the specimen in the fasting state by substituting the glycation degree of the lysine residue of the specimen measured in the process (a) into a relational expression between a glycation degree of a lysine residue of hemoglobin in blood collected from a healthy subject and a blood glucose level of blood collected from a healthy subject in the fasting state, and determining the risk for developing diabetes being relatively high in a case where the calculation value of the blood glucose level of the specimen in the fasting state is relatively higher than the evaluation criterion;
(b4) setting a calculation value of a glycation degree of a lysine residue of hemoglobin, which is obtained by substituting a glycation degree of a 13 chain N-terminal amino acid residue of hemoglobin in blood collected from the specimen into a relational expression between a glycation degree of a lysine residue of hemoglobin in blood collected from a healthy subject and a glycation degree of a 13 chain N-terminal amino acid residue of hemoglobin in blood collected from a healthy subject, as an evaluation criterion, and determining the risk for developing diabetes being relatively high in a case where the glycation degree of the lysine residue of the specimen measured in the process (a) is relatively higher than the evaluation criterion; and
(b5) setting a glycation degree of a β chain N-terminal amino acid residue of hemoglobin in blood collected from the specimen as an evaluation criterion, on the other hand, obtaining a calculation value of the glycation degree of a β chain N-terminal amino acid residue of hemoglobin of the specimen by substituting the glycation degree of the lysine residue of the specimen measured in the process (a) into a relational expression between a glycation degree of a lysine residue of hemoglobin in blood collected from a healthy subject and a glycation degree of a β chain N-terminal amino acid residue of hemoglobin in blood collected from a healthy subject, and determining the risk for developing diabetes being relatively high in a case where the calculation value of the glycation degree of the β chain N-terminal amino acid of hemoglobin is relatively higher than the evaluation criterion.

2. A method of diagnosing postprandial hyperglycemia of a specimen, wherein the method comprises the processes (c) and (d):
(c1) a process of measuring a postprandial hyperglycemia marker, wherein the postprandial hyperglycemia marker comprises hemoglobin having a glycated lysine residue, by measuring a glycation degree of a lysine residue of hemoglobin by a method of measuring comprising a step of at least one selected from the group consisting of applying a high-performance liquid chromatography method, an immunization method, an enzymatic method and an electrophoresis method with respect to a blood sample obtained from the specimen; and
(c2) a process of determining a risk for the specimen based on the postprandial hyperglycemia marker measured by the step (c1) by at least one method selected from the group consisting of (d1) to (d5):
(d1) setting a boundary value between a glycation degree of a lysine residue of hemoglobin in blood collected from a healthy subject and a glycation degree of a lysine residue of hemoglobin in blood collected from a postprandial hyperglycemia patient as an evaluation criterion, and determining the specimen being postprandial hyperglycemia in a case where the glycation degree of the lysine residue of the specimen measured in the process (c) is relatively higher than the evaluation criterion;
(d2) setting a calculation value of a glycation degree of a lysine residue of hemoglobin, which is obtained by substituting a blood glucose level of blood collected from a specimen in the fasting state into a relational expression between a glycation degree of a lysine residue of hemoglobin in blood collected from a healthy subject and a blood glucose level of blood collected from a healthy subject in the fasting state, as an evaluation criterion, and determining the specimen being postprandial hyperglycemia in a case where the glycation degree of the lysine residue of the specimen measured in the process (c) is relatively higher than the evaluation criterion;
(d3) setting a blood glucose level of blood collected from the specimen in the fasting state as an evaluation criterion, on the other hand, obtaining a calculation value of the blood glucose level of the specimen in the fasting state by substituting the glycation degree of the lysine residue of the specimen measured in the process (c) into a relational expression between a glycation degree of a lysine residue of hemoglobin in blood collected from a healthy subject and a blood glucose level of blood collected from a healthy subject in the fasting state, and determining the specimen being postprandial hyperglycemia in a case where the calculation value of the blood glucose level of the specimen in the fasting state is relatively higher than the evaluation criterion:
(d4) setting a calculation value of a glycation degree of a lysine residue of hemoglobin, which is obtained by substituting a glycation degree of a 13 chain N-terminal amino acid residue of hemoglobin in blood collected from the specimen into a relational expression between a glycation degree of a lysine residue of hemoglobin in blood collected from a healthy subject and a glycation degree of a 13 chain N-terminal amino acid residue of hemoglobin in blood collected from a healthy subject, as an evaluation criterion, and determining the specimen being postprandial hyperglycemia in a case where the glycation degree of the lysine residue of the specimen measured in the process (c) is relatively higher than the evaluation criterion; and (d5) setting a glycation degree of a 13 chain N-terminal amino acid residue of hemoglobin in blood collected from a specimen as an evaluation criterion, on the other hand, obtaining a calculation value of the glycation degree of the β chain N-terminal amino acid residue of hemoglobin of the specimen by substituting the glycation degree of the lysine residue of the specimen measured in the process (a) into a relational expression between a glycation degree of a lysine residue of hemoglobin in blood collected from a healthy subject and a glycation degree of a β chain N-terminal amino acid residue of hemoglobin in blood collected from a healthy subject, and determining the risk being relatively high in a case where a calculation value of the glycation degree of the β chain N-terminal amino acid of hemoglobin is relatively higher than the evaluation criterion.

3. A method of measuring an average blood glucose level reflecting a postprandial blood glucose level, wherein the method comprises following processes (x) and (y):

(x) a process of measuring a glycation degree of a lysine residue of hemoglobin by a method of measuring a postprandial hyperglycemia marker comprising a step of at least one selected from the group consisting of applying a high-performance liquid chromatography method, an immunization method, an enzymatic method and an electrophoresis method with respect to a blood sample obtained from a specimen, wherein the postprandial hyperglycemia marker comprises hemoglobin having a glycated lysine residue; and (y) a process of calculating the average blood glucose level reflecting a postprandial blood glucose level by substituting the glycation degree of the lysine residue of hemoglobin measured in the process (x) to a standard curve showing a relationship between a glycation degree of a lysine residue of hemoglobin and an average blood glucose level reflecting postprandial blood glucose level, wherein the standard curve is formed by plotting with respect to each of plural patients having postprandial blood glucose levels different from each other, a glycation degree of lysine residue (GHbLys %) and an average blood glucose level calculated based on blood glucose levels in blood samples collected two or more times from the same patient.

* * * * *